US009186337B2

(12) United States Patent
Baker et al.

(10) Patent No.: US 9,186,337 B2
(45) Date of Patent: Nov. 17, 2015

(54) **LYSINE DEMETHYLASE INHIBITORS FOR DISEASES AND DISORDERS ASSOCIATED WITH *HEPADNAVIRIDAE***

(75) Inventors: Jonathan Alleman Baker, Holladay, UT (US); Matthew Colin Thor Fyfe, Chipping Norton (GB)

(73) Assignee: Oryzon Genomics S.A., Barcelona (ES)

( * ) Notice: Subject to any disclaimer, the term of this patent is extended or adjusted under 35 U.S.C. 154(b) by 0 days.

(21) Appl. No.: 13/580,710

(22) PCT Filed: Feb. 24, 2011

(86) PCT No.: PCT/US2011/026140
§ 371 (c)(1),
(2), (4) Date: Jan. 4, 2013

(87) PCT Pub. No.: WO2011/106573
PCT Pub. Date: Sep. 1, 2011

(65) Prior Publication Data
US 2013/0095067 A1   Apr. 18, 2013

Related U.S. Application Data

(60) Provisional application No. 61/338,935, filed on Feb. 24, 2010, provisional application No. 61/458,786, filed on Nov. 30, 2010.

(51) Int. Cl.
| | | |
|---|---|---|
| *A61K 31/131* | (2006.01) | |
| *A61K 31/135* | (2006.01) | |
| *A61K 31/165* | (2006.01) | |
| *A61K 31/15* | (2006.01) | |
| *A61K 38/21* | (2006.01) | |
| *A61K 45/06* | (2006.01) | |
| *A61K 31/137* | (2006.01) | |

(52) U.S. Cl.
CPC ............ *A61K 31/135* (2013.01); *A61K 31/131* (2013.01); *A61K 31/137* (2013.01); *A61K 31/15* (2013.01); *A61K 31/165* (2013.01); *A61K 38/21* (2013.01); *A61K 45/06* (2013.01)

(58) Field of Classification Search
CPC . A61K 31/131; A61K 31/135; A61K 31/165; A61K 31/137
See application file for complete search history.

(56) References Cited

U.S. PATENT DOCUMENTS

| | | | |
|---|---|---|---|
| 3,106,578 | A | 10/1963 | Kaiser et al. |
| 3,365,458 | A | 1/1968 | Biel et al. |
| 3,471,522 | A | 10/1969 | Biel et al. |
| 3,532,712 | A | 10/1970 | Biel et al. |
| 3,758,684 | A | 9/1973 | Elion et al. |
| 4,409,243 | A | 10/1983 | Lieb |
| 4,522,811 | A | 6/1985 | Eppstein et al. |
| 4,530,901 | A | 7/1985 | Weissmann |
| 6,043,393 | A | 3/2000 | de Meijere et al. |
| 6,211,244 | B1 | 4/2001 | Van Wagenen et al. |
| 6,337,074 | B1 | 1/2002 | Marsden et al. |
| 6,809,120 | B1 | 10/2004 | Warrington et al. |
| 7,399,825 | B2 | 7/2008 | Lipps et al. |
| 7,611,704 | B2 | 11/2009 | Thorpe et al. |
| 7,628,993 | B2 | 12/2009 | Vilalta et al. |
| 7,799,782 | B2 | 9/2010 | Munson et al. |
| 8,524,717 | B2 | 9/2013 | Guibourt et al. |
| 8,722,743 | B2 | 5/2014 | Ortega-Munoz et al. |
| 8,859,555 | B2 | 10/2014 | Ortega Munoz et al. |
| 8,946,296 | B2 | 2/2015 | Ortega Munoz et al. |
| 8,993,808 | B2 | 3/2015 | Guibourt et al. |
| 9,006,449 | B2 | 4/2015 | Fyfe et al. |
| 2003/0008844 | A1 | 1/2003 | Spero et al. |
| 2003/0236225 | A1 | 12/2003 | Protopopova et al. |
| 2004/0019117 | A1 | 1/2004 | Protopopova et al. |
| 2004/0033986 | A1 | 2/2004 | Protopopova et al. |
| 2004/0048802 | A1 | 3/2004 | Ripka et al. |
| 2004/0132820 | A1 | 7/2004 | Gosselin et al. |
| 2004/0147741 | A1 | 7/2004 | Sundermann et al. |
| 2004/0162287 | A1 | 8/2004 | Sundermann et al. |

(Continued)

FOREIGN PATENT DOCUMENTS

| | | |
|---|---|---|
| EP | 1193268 | 4/2002 |
| EP | 1704859 | 9/2006 |

(Continued)

OTHER PUBLICATIONS

Ahmed et al, "Ticagrelor: a new reversible oral antiplatelet agent" Int Research Journal of Pharmacy, 2010, 1(1), 62-69.
Arya et al, "Synthesis of 5H-dibenzo[a,d]cycloheptene derivatives with diverse biological activities", Indian J Chemistry B, 1978, 16B,220-225.
Bar-Am et al, "Regulation of Bcl-2 family proteins, neurotrophic factors, and APP processing in the neurorescue activity of propargylamine". FASEB J, 2005, 19(13),1899-1901.
Barlesi et al, "Global histone modifications predict prognosis of resected non small-cell lung cancer",J Clin Oncol,2007,25, 4358-4364.

(Continued)

*Primary Examiner* — Robert Landsman
*Assistant Examiner* — Bruce D Hissong
(74) *Attorney, Agent, or Firm* — Finnegan, Henderson, Farabow, Garrett & Dunner, LLP

(57) ABSTRACT

The present invention provides for the treatment or prevention of Hepadnaviridae infection and disease caused by Hepadnaviridae infection. In particular, the invention provides compositions and methods that affect the ability of Hepadnaviridae to utilize the host's cellular machinery as part of the virus' lifecycle. The invention relates to the discovery that interfering with the normal ability of viruses to utilize the host cell machinery with LSD1 inhibitors reduces HBV replication. Thus, the treatment and prevention of Hepadnaviridae infection and disease caused by Hepadnaviridae according to the invention comprises administering to an individual in need of treatment, a therapeutically effective amount of a LSD1 inhibitor. The individual in need of treatment can be a human or, e.g., another mammal.

20 Claims, 3 Drawing Sheets

(56) References Cited

U.S. PATENT DOCUMENTS

| | | |
|---|---|---|
| 2004/0176469 A1 | 9/2004 | Thomas |
| 2004/0229872 A1 | 11/2004 | Friderichs et al. |
| 2004/0254158 A1 | 12/2004 | Qiao et al. |
| 2005/0009832 A1 | 1/2005 | Sun et al. |
| 2005/0154056 A1 | 7/2005 | Yang et al. |
| 2006/0116370 A1 | 6/2006 | Dollinger et al. |
| 2006/0148904 A1 | 7/2006 | Protopopova et al. |
| 2006/0211709 A1 | 9/2006 | Buhr et al. |
| 2006/0270673 A1 | 11/2006 | Duggan et al. |
| 2006/0275366 A1 | 12/2006 | Malcom et al. |
| 2006/0287287 A1 | 12/2006 | Gerritz et al. |
| 2007/0213338 A1 | 9/2007 | Lebsack et al. |
| 2008/0139665 A1 | 6/2008 | Schuele et al. |
| 2008/0242698 A1 | 10/2008 | Flor et al. |
| 2008/0269228 A1 | 10/2008 | Moore et al. |
| 2009/0203750 A1 | 8/2009 | Kozikowski et al. |
| 2009/0247530 A1 | 10/2009 | Nolte et al. |
| 2010/0016262 A1 | 1/2010 | Mehal et al. |
| 2010/0240649 A1 | 9/2010 | Zhang |
| 2010/0292225 A1 | 11/2010 | Chamoin et al. |
| 2010/0324147 A1 | 12/2010 | McCafferty et al. |
| 2012/0202810 A1 | 8/2012 | Nolte et al. |
| 2013/0197095 A1 | 8/2013 | Nolte et al. |

FOREIGN PATENT DOCUMENTS

| | | |
|---|---|---|
| EP | 1741708 | 1/2007 |
| EP | 2233495 | 9/2010 |
| GB | 1307341 | 2/1973 |
| JP | 2001354563 | 12/2001 |
| SU | 230169 | 10/1968 |
| WO | WO94/27947 | 12/1994 |
| WO | WO96/38141 | 12/1996 |
| WO | WO98/18459 | 5/1998 |
| WO | WO99/05142 | 2/1999 |
| WO | WO99/05143 | 2/1999 |
| WO | WO99/31072 | 6/1999 |
| WO | WO99/54440 | 10/1999 |
| WO | WO99/67203 | 12/1999 |
| WO | WO00/34283 | 6/2000 |
| WO | WO01/92264 | 12/2001 |
| WO | WO02/079152 | 10/2002 |
| WO | WO03/087064 | 10/2003 |
| WO | WO03/093297 | 11/2003 |
| WO | WO03/096989 | 11/2003 |
| WO | WO2004/020415 | 3/2004 |
| WO | WO2004/055010 | 7/2004 |
| WO | WO2004/062601 | 7/2004 |
| WO | WO2004/065367 | 8/2004 |
| WO | WO2004/072086 | 8/2004 |
| WO | WO2005/009941 | 2/2005 |
| WO | WO2005/023761 | 3/2005 |
| WO | WO2005/025558 | 3/2005 |
| WO | WO2005/037843 | 4/2005 |
| WO | WO2005/058808 | 6/2005 |
| WO | WO2005/058883 | 6/2005 |
| WO | WO2005/058884 | 6/2005 |
| WO | WO2005/103003 | 11/2005 |
| WO | WO2006/071608 | 7/2006 |
| WO | WO2006/087206 | 8/2006 |
| WO | WO2007/000248 | 1/2007 |
| WO | WO2007/005896 | 1/2007 |
| WO | WO2007/015824 | 2/2007 |
| WO | WO2007/025144 | 3/2007 |
| WO | WO2007/025709 | 3/2007 |
| WO | WO2007/021839 | 7/2007 |
| WO | WO2007/106016 | 9/2007 |
| WO | WO2007/134799 | 11/2007 |
| WO | WO2008/033466 | 3/2008 |
| WO | WO2008/116156 | 9/2008 |
| WO | WO2008/127734 | 10/2008 |
| WO | WO2009/001132 | 12/2008 |
| WO | WO2009/023179 | 2/2009 |
| WO | WO2009/039134 | 3/2009 |
| WO | WO2009/052078 | 4/2009 |
| WO | WO2009/097278 | 8/2009 |
| WO | WO2009/109991 | 9/2009 |
| WO | WO2009/117515 | 9/2009 |
| WO | WO2009/145856 | 12/2009 |
| WO | WO2009/153197 | 12/2009 |
| WO | WO2010/011845 | 1/2010 |
| WO | WO2010/014921 | 2/2010 |
| WO | WO2010/030592 | 3/2010 |
| WO | WO2010/043721 | 4/2010 |
| WO | WO2010/084160 | 7/2010 |
| WO | WO2010/085749 | 7/2010 |
| WO | WO2010/099527 | 9/2010 |
| WO | WO2010/139784 | 12/2010 |
| WO | WO2010/143582 | 12/2010 |
| WO | WO2011/022489 | 2/2011 |
| WO | WO2011/031934 | 3/2011 |
| WO | WO2011/035941 | 3/2011 |
| WO | WO2011/042217 | 4/2011 |
| WO | WO2011/057262 | 5/2011 |
| WO | WO2011/106105 | 9/2011 |
| WO | WO2011/106106 | 9/2011 |
| WO | WO2011/113005 | 9/2011 |
| WO | WO2011/131576 | 10/2011 |
| WO | WO2011/131697 | 10/2011 |
| WO | WO2011/132083 | 10/2011 |
| WO | WO2012/001531 | 1/2012 |
| WO | WO2012/013727 | 2/2012 |
| WO | WO2012/013728 | 2/2012 |
| WO | WO2012/034116 | 3/2012 |
| WO | WO2012/042042 | 4/2012 |
| WO | WO2012/045883 | 4/2012 |
| WO | WO2012/072713 | 6/2012 |
| WO | WO2012/107498 | 8/2012 |
| WO | WO2012/107499 | 8/2012 |
| WO | WO2012/135113 | 10/2012 |
| WO | WO2012/156531 | 11/2012 |
| WO | WO2012/156537 | 11/2012 |
| WO | WO2013/057320 | 4/2013 |
| WO | WO2013/057322 | 4/2013 |

OTHER PUBLICATIONS

Benelkebir et al, "Enantioselective synthesis of tranylcypromine analogues as lysine demethylase (LSD1) inhibitors", Bioorg Med Chem. 2011, 19(12),3709-3716.

Biljak et al,"Platelet count, mean platelet volume and smoking status in stable chronic obstructive pulmonary disease", Platelets, 2011,22(6), 466-70.

Binda et al, "Biochemical, structural, and biological evaluation of tranylcypromine derivatives as inhibitors of histone demethylases LSD1 and LSD2". J Am Chem Soc,2010, 132(19),6827-6833.

Bisi et al, "Multidrug resistance reverting activity and antitumor profile of new phenothiazine derivatives", Bioorg Med Chem, 2008, 16(13), 6474-6482.

Boilard et al, "Platelets amplify inflammation in arthritis via collagen-dependent microparticle production", Science, 2010,327(5965), 580-583.

Bolesov et al, "Cyclopropanes and cyclobutanes LXIX", Zhurnal Organicheskoi Khimii (English Translation), 1974, 10(10), 2122-2128.

Bolesov et al, "Cyclopropanes and cyclobutanes LXVII. N-mono and N,N-disubstituted 1-amino-2-phenylcyclopropanes",Zhurnal Organicheskoi Khimii (English Translation), 1974, 10(6), 1678-84.

Brand and Perrimon, "Targeted gene expression as a means of altering cell fates and generating dominant phenotypes", 1993, Development, 118, 401-415.

Brydon et al, "Platelets, coronary heart disease and stress", Brain, Behavior and Immunity,2006, 20(2), 113-119.

Burakova et al, "N- and O-alkylation of 3-indolylcyclopropylacetic acid derivatives", Russian Chemical Bulletin, 2002, 51(10) 1829-1840.

Burk et al, "Cognitive deficits in spinocerebellar ataxia 2", Brain, 1999,122(4), 769-777.

Cakmak et al, "Platelets: indicator of inflammation in COPD", Int J Med Med Sci, 2009, 1 (5), 227-229.

(56) References Cited

OTHER PUBLICATIONS

Calogero et al, "Inhibition of cell growth by EGR-1 in human primary cultures from malignant glioma",Cancer Cell International,2004,4, 1.
Casero et al, "Recent advances in the development of polyamine analogues as antitumor agents", J Med Chem, 2009, 52(15),4551-4573.
Chen et al, "Association in insulin resistance and hematologic parameters: study of a middle-aged and elderly chinese population in Taiwan", J Chin Med Assoc,2006, 69(6), 248-253.
Chimenti et al "Synthesis, Stereochemical Identification, and Selective Inhibitory Activity against Human Monoamine Oxidase-B of 2-Methylcyclohexylidene-(4-arylthiazol-2-yl)hydrazones". (2008) J. Med. Chem. 51 (16), 4874-4880.
Choi et al "Histone demethylase LSD1 is required to induce skeletal muscle differentiation by regulating myogenic factors" (2010) Biochemical and Biophysical Research Communications 401(3), 327-332.
Choo et al, "Genetic organization and diversity of the hepatits C virus", Proc Natl Acad Sci, 1991, 88,2451-2455.
Culhane et al, A mechanism-based inactivator for histone demethylase LSD1, J Am Chem Soc, 2006, 128(14), 4536-4537.
Culhane et al, "Comparative analysis of small molecules and histone substrate analogues as LSD1 lysine demethylase inhibitors", J Am Chem Soc, 2010,132(9).3164-3176.
Danese et al, "Platelets in inflammatory bowel disease: clinical, pathogenic and therapeutic implications", Am J Gastroenterol, 2004,99(5), 938-45.
Di Stefano et al, Mutation of *Drosophila* Lsd1 disrupts H3-K4 methylation, resulting in tissue-specific defects during development, Curr Biol,2007, 17(9), 808-12.
East et al, "An orally bioavailable positive allosteric modulator of the mGlu4 receptor with efficacy in an animal model of motor dysfunction", Bioorg Med Chem Lett, 2010, 20(16), 4901-5.
Ellis et al, "Expression of *Drosophila* glass protein and evidence for negative regulation of its activity in non-neuronal cells by another DNA-binding protein",Development,1993, 119, 855-865.
Elsheikh et al "Global histone modifications in breast cancer correlate with tumor phenotypes, prognostic factors and patient outcome", Canc Res, 2009,69, 3802-3809.
Erazo et al, "Varicella-zoster virus open reading frame 66 protein kinase is required for efficient viral growth in primary human corneal stromal fibroblast cells", J Virol. 2008.82, 7653-7665.
Faler et al, "The Kulinkovich reaction in the synthesis of constrained N,N-dialkyl neurotransmitter analogues", Organic Letters 2007,9(10),1987-1990.
Ferlay et al, "Estimates of the cancer incidence and mortality in Europe in 2006", Annals of Oncology 2007,18(3), 581-92.
Ferraro et al, "EGR1 predicts PTEN and survival in patients with non-small-cell lung cancer", J Clin Oncol, 2005, 23(9), 1921-26.
Fischer et al, "Recovery of learning and memory is associated with chromatin remodelling", Nature, 2007,447, 178-182.
Forneris et al "LSD1: oxidative chemistry for multifaceted functions in chromatin Regulation." Trends in Biochemical Sciences 2008,33(4), 181-189.
Gawaz et al, "Platelets in inflammation and atherogenesis", J Clin Invest, 2005,115(12), 3378-3384.
Gooden et al, "Facile synthesis of substituted trans-2-arylcyclopropylamine inhibitors of the human histone demethylase LSD1 and monoamine oxidases A and B". Bioorg Med Chem Lett 2008, 18(10), 3047-51.
Han et al "Modulation of breast cancer resistance protein (BCRP/ABCG2) by non-basic chalcone analogues" Eur. J. Pharma. 2008, 35(1-2) 30-41.
Han et al, "Antidepressants reveal differential effect against 1-methyl-4-phenylpyridinium toxicity in differentiated PC12 cells", Eur J Pharmacol, 2009, 604 (1-3),36-44.
Hayami et al, "Overexpression of LSD1 contributes to human carcinogenesis through chromatin regulation in various cancers", Int J Cancer, 2011, 128(3), 574-86.

Hruschka et al, "Fluorinated phenylcyclopropylamines. Part 5:Effect of electron-withdrawing or- donating aryl substituents on the inhibition of monoamine oxidases A and B by 2-aryl-2-fluoro-cyclopropylamines", Bioorg Med Chem,2008, 16(15), 7148-7166.
Huang et al, "Novel oligoamine analogues inhibit lysine-specific demethylase 1 (LSD1) and induce re-expression of epigeneticall silenced genes",Clin Cancer Res,2009, 15(23), 7217-28.
Huang et al, "p53 is regulated by the lysine demethylase LSD1",Nature,2007,449, 105-108.
Huang et al,"Inhibition of lysine-specific demethylase 1 by polyamine analogues results in reexpression of aberrantly silenced genes", PNAS,2007, 104(19). 8023-8028.
Jackson et al, "Polyglutamine-expanded human Huntingtin transgenes induce degeneration of *Drosophila* photoreceptor neurons", Neuron, 1998, 21, 633-642.
Kahl et al,"Androgen receptor coactivators lysine-specific histone demethylase 1 and four and a half LIM domain protein 2 predict risk of prostate cancer recurrence", Cancer Res,2006,66 (23), 11341-11347.
Kaiser et al, "2-substituted cyclopropylamines. I. Derivatives and analogs of 2-Phenylcyclopropylamine", J Med Pharm Chem (ACS), 1962, 5, 1243-1265.
Kiefmann et al, "Red blood cells induce hypoxic lung inflammation", Blood, 2008,111(10),5205-14.
Kim et al, "Flavin chemical models for monoamine oxidase inactivation by cyclopropylamines, α-silylamines, and hydrazines", J Am Chem Soc 1995, 117, 100-105.
Kinzel et al, "Identification of MK-5710 ((8aS)-8a-methyl-1,3-dioxo-2-[(1S,2R)-2-phenylcyclopropyl]-N-(1-phenyl-1H-pyrazol-5-yl)hexahydro-imidazo[1,5-a]pyrazine-7-(1H)-carboxamide), a potent smoothened antagonist for use in Hedgehog pathway dependent malignancies. Part 2", Bioorg Med Chem Lett 2011, 21(15), 4429-4435.
Kornerup et al, "The role of platelets in the pathophysiology of asthma" Platelets, 2007,18(5), 319-28.
Krieger et al, "Enhancement of hepatitis C virus RNA replication by cell culture-adaptive mutations", J Virol, 2001,75, 4614-4624.
Lan et al "Mechanisms involved in the regulation of histone lysine demethylases", Current Opinion in Cell Biology, 2008,20, 316-325.
Lee et al, "Combinatorial lead optimization of [1,2]-diamines based on ethambutol as potential antituberculosis preclinical candidates", J Comb Chem, 2003, 5(2), 172-187.
Lee et al, "Histone H3 lysine 4 demethylation is a target of nonselective antidepressive medications",Chem Biol. 2006,13(6), 563-567.
Li et al, "Association between inflammatory mediators and angiographic morphologic features indicating thrombus formation in patients with acute myocardial infarction", Chin Med J. 2009, 122(15), 1738-42.
Liang et al, "Inhibition of the histone demethylase LSD1 blocks alpha-herpesvirus lytic replication and reactivation from latency",Nat Med, 2009,15 (11), 1312-1317.
Lim et al, "Lysine-specific demethylase 1(LSD1) is highly expressed in ER-negative breast cancers and a biomarker predicting aggressive biology", Carcinogenesis,2010, 31(3), 512-20.
Lucerna et al, "Sustained expression of early growth response protein-1 blocks angiogenesis and tumor growth",Cancer Research,2006, 66,6708-6713.
Lupu Roxana, "Up-to-date in the hematological malignancies treatment", Maedica, 2006,1(1), 63-65.
Maclay et al, "Increased platelet activation in patients with stable and acute exacerbation of COPD", Thorax, 2011,66(9); 769-74.
Mannaioni et al, "Platelets and inflammation: role of platelet-derived growth factor, adhesion molecules and histamine", Inflamm Res, 1997,46(1), 4-18.
McNicol et al, "Beyond hemostasis: the role of platelets in inflammation, malignancy and infection",Cardiovascular & Haematological Disorders-Drug Targets, 2008,8, 99-117.
Meanwell, "Synopsis of some recent tactical application of bioisosteres in drug design", J Med Chem, 2011, 54(8),2529-91.
Metzger et al. "LSD1 demethylates repressive histone marks to promote androgen-receptor-dependent transcription",Nature,2005, 437(7057),436-9.

(56) References Cited

OTHER PUBLICATIONS

Mimasu et al "Crystal structure of histone demethylase LSD1 and tranylcypromine at 2.25 Å" Biochemical and Biophysical Research Communications ,2008,366, 15-22.
Mimasu et al, "Structurally designed trans-2-phenylcyclopropylamine derivatives potently inhibit histone demethylase LSD1/KDM1", Biochemistry,2010,49(30), 6494-6503.
Moritani et al, "Activation of platelets in brochial asthma", Chest, 1998,113, 452-458.
Nabil Aboul-Enein et al, "Synthesis of some 4-substituted amino-1-methylpiperidines structurally related to antihistaminics", Pharmaceutica Acta Helvetiae, 1973, 48(3): 151-156.
Neelamegan et al, "Brain-penetrant LSD1 inhibitors can block memory consolidation", ACS Chem Neurosci, 2012, 3(2), 120-128.
Ogasawara et al, "Synthesis and biological activity of optically active NCL-1, a lysine-specific demethylase 1 selective inhibitor", Bioorg Med Chem, 2011, doi:10.1016/j.bmc.2010.12.024.
O'Sullivan et al, "The inflammatory role of platelets in cystic fibrosis", Am J Respir Crit Care Med, 2006,173, 483-90.
Pannala et al "Synthesis and structure-activity relationship of 4-(2-aryl-cycloprpylamino)-quinoline-3-carbonitriles as EGFR tyrosine kinase inhibitors". Bioorg & Med Chem Lett , 2007,17 (21), 5978-5082.
Pitchford et al, "Platelet P-selectin is required for pulmonary eosinophil and lymphocyte recruitment in a murine model of allergic inflammation", Blood, 2005,105, 2074-2081.
Pollock et al, Lysine-specific histone demethylase 1 inhibitors control breast cancer proliferation in ERalpha-dependent and -independent manners, ACS Chem Biol 2012,7,1221-1231.
Ravina et al, "The relationship between CAG repeat length and clinical progression in Huntington's disease", Movement Disorders,2008,23(9), 1223-7.
Reddy et al, "Role of lysine-specific demethylase 1 in the proinflammatory phenotype of vascular smooth muscle cells of diabetic mice",Circ Res,2008, 103, 615-23.
Riley et al, "Absolute configuration of (+)- and (−)-trans-2-phenylcyclopropylamine hydrochloride",J.Med Chem, 1972,15(11), 1187-1188.
Rinder et al, "Correlation of thrombosis with increased platelet turnover in thrombocytosis", Blood, 1998,91(4), 1288-1294.
Schmidt et al,"trans-2-phenylcyclopropylamine is a mechanism-based inactivator of the histone demethylase LSD1", Biochemistry, 2007,46(14),4408-4416.
Schulte et al, "Lysine-specific demethylase 1 is strongly expressed in poorly differentiated neuroblastoma: implications for therapy", Cancer Res,2009,69(5),2065-71.
Scoumanne et al "Protein methylation: a new mechanism of p53 tumor suppressor regulation" Histol Histopathol 2008,23, 1143-1149.
Scoumanne et al, "The lysine-specific demethylase 1 is required for cell proliferation in both p53-dependent and -independent manners", J Biol Chem, 2007,282(21), 15471-5.
Seligson et al, "Global histone modification patterns predict risk of prostate cancer recurrence",Nature, 2005,435,1262-1266.
Seligson et al,"Global levels of histone modifications predict prognosis in different cancers" ,Am J Path, 2009,174,1619-28.
Sharma et al, "(Bis)urea and (bis)thiourea inhibitors of lysine-specific demethylase 1 as epigenetic modulators", J Med Chem, 2010,53(14), 5197-5212.
Shi et al,"Histone demethylation mediated by the nuclear amine oxidase homolog LSD1", Cell, 2004,119,941-953.
Shi, "Histone lysine demethylases: emerging roles in development, physiology and disease", Nature Reviews Genetics 2007, 8:829-833.
Stephens et al, "The determination of the absolute configurations of chiral molecules using vibrational circular dichroism (VCD) spectroscopy",Chirality, 2008,20(5), 643-663.
Stoffel et al, "Leukocyte count and risk of thrombosis in patients undergoing haematopoietic stem cell transplantation or intensive chemotherapy",Thromb Haemost, 2010,103(6), 1228-32.

Stratmann et al, "Pathobiology and cell interactions of platelets in diabetes", Diabetes & Vascular Disease Research,2005, 2(1), 16-23.
Szewczuk et al, "Mechanistic analysis of a suicide inactivator of histon demethylase LSD1", Biochemistry, 2007,46, 6892-6902.
Tamagawa-Mineoka et al, "Elevated platelet activation in patients with atopic dermatitis and psoriasis: increased plasma levels of beta-thromboglobulin and platelet factor 4", Allergology International,2008, 57, 391-396.
Taylor et al,"Roscovitine, a cyclin-dependent kinase inhibitor, prevents replication of varicella-zoster virus", J Virol, 2004,78, 2853-2862.
Thaulow et al, "Blood platelet count and function are related to total and cardiovascular death in apparently healtht men", Circulation, 1991,84, 613-617.
Ueda et al, "Identification of cell-active lysine specific demethylase 1-selective inhibitors",J Am Chem Soc, 2009,131(48), 17536-17537.
Vagner et al, "Peptidomimetics, a synthetic tool of drug discovery", Current Opinion on Chemical Biology, 2008, 12:292-296.
Wagner et al, "Platelets in inflammation and thrombosis", Arteriosclerosis, Thrombosis and Vascular Biology, 2003,23, 2131-2137.
Wang et al, Novel histone demethylase LSD1 inhibitors selectively target cancer cells with pluripotent stem cell properties, Cancer Research, 2011, 71(23):7238-49.
Wang et al "LSD1 is a Subunit of the NuRD Complex and Targets the Metastasis Programs in Breast Cancer" Cell 2009, 138, 660-672.
Wang et al, "The lysine demethylase LSD1 (KDM1) is required of maintenance of global DNA methylation", Nature Genetics, 2009,41(1), 125-129.
Weinreb et al, "Novel neuroprotective mechanism of action of rasagiline is associated with its propargyl moiety: interaction of Bcl-2 family memebers with PKC pathway", Ann NY Acad Sci, 2005,1053, 348-55.
Wermuth, "Molecular variations based on isosteric replacements", The Practice of Medicinal Chemistry (2nd edition), Academic Press, London, 2003, pp. 189-214.
Westland et al , "N-substituted derivatives of 2-aminoethanethiol and 2-hydraxinoethanethiol", JMedChem 1968, 11(4),824-829.
Whitlow et al,"Recruitment of the transcriptional coactivator HCF-1 to viral immediate-early promotes during initiation of reactivation from latency of herpes simplex virus type 1", J Virol, 2009,83(18):9591-5.
Willoughby et al, "Platelets and cardiovascular disease",Eur J Cardiovasc Nursing,2002,1, 273-288.
XP002568777 Database chemcats, database accession No. 2088922753, order No. kbsb-0063197, Aurora screening library, Aug. 20, 2009.
Yang et al "Structural Basis for the Inhibition of the LSD1 Histone Demethylase by the Antidepressant trans-2-Phenylcyclopropylamine" Biochemistry 2007,46 (27), 8058-8065.
Yang et al "Structural basis of histone demethylation by LSD1 revealed by suicide inactivation" Nature Structural & Molecular Biology 2007, 14(6), 535-539.
Yoshida et al, "Fluorinated phenylcyclopropylamines. Part 3: inhibition of monoamine oxidase A and B",Bioorg Med Chem,2004,12(10),2645-2652.
Youdim et al, "Bifunctional drug derivatives of MAO-B inhibitor rasagiline and iron chelator VK-28 as a more effective approach to treatment of brain ageing and ageing neurodegenerative diseases", Mechanisms of Ageing and Development, 2005, 126: 317-326.
F. Zaragoza Dörwald "Side reactions in Organic Synthesis: a guide to successful synthesis design" Wiley-VCH Verlag GmbH & Co, KGaA, Wilenheim, Chapter 1, 2005.
Zirkle et al, "2-substituted cyclopropylamines. II. Effect of structure upon monamine oxidase-inhibitory activity as measure in vivo by potentiation of tryptamine convulsions", J Med Pharm Chem (ACS), 1962, 5, 1265-84.
"Definition of Cancer"—MedicineNetcom Medical references for patients, http://www.medterms.com, 2005.
Johnson et al, CAPLUS, Document No. 157:576967, "Preperation of cyclopropylamines as LSD1 inhibitors in the treatment of cancer", 2012.

(56) References Cited

OTHER PUBLICATIONS

Delorme et al, HCAPLUS, Document No. 132:49802, "Preperation of 1-(N-substituted aminomethyl)-4-guanidinomethylcyclohexanes useful in pain management". 1999.
CAS Registry No. RN220351-33-7, entered STN Mar. 11, 1999.
CAS Registry No. RN844655-03-4, entered STN Mar. 9, 2005.
CAS Registry No. RN846596-02-9, entered STN Mar. 22, 2005.
CAS Registry No. RN848204-13-7, entered STN Apr. 11, 2005.
CAS Registry No. RN848732-87-6, entered STN Apr. 19, 2005.
CAS Registry No. RN848742-47-2, entered STN Apr. 19, 2005.
CAS Registry No. RN848753-47-9, entered STN Apr. 19, 2005.
CAS Registry No. RN903487-42-3, entered STN Aug. 23, 2006.
CAS Registry No. RN918305-55-2, entered STN Jan. 24, 2007.
CAS Registry No. RN959071-98-8, entered STN Dec. 20, 2007.
CAS Registry No. RN1026299-47-7, entered STN Jun. 8, 2008.
CAS Registry No. RN1157140-28-7, entered STN Jun. 14, 2009.
CAS Registry No. RN1218057-33-0, entered STN Apr. 11, 2010.
CAS Registry No. RN1247564-27-7, entered STN Oct. 27, 2010.
CAS Registry No. RN1247717-42-5, entered STN Oct. 27, 2010.
CAS Registry No. RN1247999-77-4, entered STN Oct. 28, 2010.
CAS Registry No. RN1248611-33-7, entered STN Oct. 29, 2010.
CAS Registry No. RN1248913-30-5, entered STN Nov. 1, 2010.
CAS Registry No. RN1248971-98-3, entered STN Nov. 1, 2010.
CAS Registry No. RN1250045-89-6, entered STN Nov. 1, 2010.
CAS Registry No. RN1250199-20-2, entered STN Nov. 1, 2010.
CAS Registry No. RN1250332-49-0, entered STN Nov. 1, 2010.
CAS Registry No. RN1251130-23-0, entered STN Nov. 3, 2010.
Co-pending U.S. Appl. No. 13/138,143, filed Jul. 11, 2011.
Co-pending U.S. Appl. No. 13/497,994, filed Mar. 23, 2012.
Co-pending U.S. Appl. No. 13/500,687, filed Apr. 6, 2012.
Co-pending U.S. Appl. No. 13/580,553, filed Aug. 22, 2012.
Co-pending U.S. Appl. No. 13/812,366, filed Jan. 25, 2013.
Co-pending U.S. Appl. No. 13/812,386, filed Jan. 25, 2013.
Co-pending U.S. Appl. No. 13/876,485, filed Mar. 28, 2013.
Co-pending U.S. Appl. No. 13/877,919, filed Apr. 5, 2013.
Co-pending U.S. Appl. No. 13/983,844, filed Aug. 6, 2013.
Co-pending U.S. Appl. No. 14/118,323, filed Nov. 18, 2013.
Co-pending U.S. Appl. No. 14/118,330, filed Nov. 18, 2013.
Co-pending U.S. Appl. No. 14/096,557, filed Dec. 4, 2013.
Co-pending U.S. Appl. No. 14/184,745, filed Feb. 19, 2014.
Co-pending U.S. Appl. No. 14/228,083, filed Mar. 27, 2014.
Co-pending U.S. Appl. No. 14/352,719, filed Apr. 18, 2014.
Co-pending U.S. Appl. No. 14/352,711, filed Apr. 18, 2014.
International Search Report and Written Opinion received in the corresponding International Patent Application No. PCT/US2011/026140, dated Nov. 30, 2011.
Co-pending U.S. Appl. No. 14/480,765, filed Sep. 9, 2014.
Co-pending U.S. Appl. No. 14/627,333, filed Feb. 20, 2015.
Co-pending U.S. Appl. No. 14/640,395, filed Mar. 6, 2015.
Co-pending U.S. Appl. No. 14/675,990, filed Apr. 1, 2015.

LYSINE DEMETHYLASE INHIBITORS FOR DISEASES AND DISORDERS ASSOCIATED WITH *HEPADNAVIRIDAE*

PRIORITY CLAIM

This application claims the benefit of the filing date of U.S. Provisional Patent Application Ser. No. 61/458,786, filed Nov. 30, 2010, for "LYSINE DEMETHYLASE INHIBITORS FOR DISEASES AND DISORDERS ASSOCIATED WITH HEPADNAVIRIDAE," and U.S. Provisional Patent Application Ser. No. 61/338,935, filed Feb. 24, 2010, for "INHIBITORS FOR ANTIVIRAL USE," the entire disclosure of each of which is hereby incorporated herein by this reference.

TECHNICAL FIELD

The invention relates to methods and compositions for the treatment or prevention diseases and disorder associated with Hepadnaviridae and in particular hepatitis B virus.

BACKGROUND

Viral infection of humans is a major health problem. Combating viral infection has proven to be highly effective in some cases like smallpox where the disease was essentially eradicated with the advent of the smallpox vaccination. Other viral infections have been much more difficult to fight. Hepatitis B and C, human immunodeficiency virus (HIV), and herpes viruses are just a few prominent members of a list of viruses that pose significant health threats worldwide. Treatments available for these viruses are associated with adverse side-effects. In some cases the viruses mutate and become resistant to a particular treatment. Accordingly, there is a clear need for new antiviral treatments.

Hepatitis virus B (HBV) is estimated to be responsible for approximately 4000-5000 deaths each year in the United States alone. The problem is substantially greater in the rest of the world and accounts for about 1 million deaths worldwide each year.

According to the Center for Disease Control, about one in twenty people in the United States will get infected with HBV. About two billion people worldwide have been infected with HBV, and 350 million of those have chronic infection. It is estimated that upwards of 10% of the population of the developing world (large parts of Asia, the Pacific, and sub-Saharan Africa) are chronically infected with HBV. Chronically infected individuals are at a much greater risk for hepatocellular carcinoma (liver cancer) and cirrhosis of the liver. Liver cancer caused by HBV is one of the leading causes of death in men by cancer in the developing world. By any analysis, HBV is one of the more serious health problems facing the world. HBV is transmitted by contact with blood or other body fluids of an infected person and is similar to the human immunodeficiency virus in that sense, but it is about two orders of magnitude more infectious than HIV. The main paths of transmission are from mother to infant at birth, child-to-child, unsafe injections and transfusions, and unsafe sexual contact.

HBV was probably first reported in the late 19th century in shipyard workers in Bremen who had been vaccinated against smallpox. Over the next one hundred years the association of hepatitis with the use of needles and syringes used for treating diseases like syphilis, diabetes, and the administration of vaccines for yellow fever, led scientists to discover HBV. Eventually a vaccine was developed from a viral envelope protein that was purified from the plasma of individuals with a chronic HBV infection. Later, a recombinant system was used to produce the protein used in the vaccines because the original source of the vaccine was those individuals infected with HBV and this same population was at high-risk for HIV infection.

The HBV vaccine was shown to be about 95% effective in preventing chronic infection in individuals if they were not previously infected. Unfortunately, the HBV vaccine does not cure the disease and there is a need from new treatments.

HBV is a circular DNA virus with double stranded and single stranded DNA with a genome of about 2300 nucleotides long for the full length strand and from about 1700-2800 nucleotides long for the short length strand.

After cell entry via attachment of HBV to host receptors and endocytosis, relaxed circular HBV DNA is transported to the nucleus where it is "repaired" to form covalently closed circular DNA (cccDNA). HBV DNA is replicated through an RNA intermediate.

This discovery now provides an entirely new class of HBV antivirals useful for treating and preventing HBV infection and related diseases like viral hepatitis and liver cancer.

One long standing difficult goal in antiviral research has been the search of host cell factors that can be target for treating and preventing viral infection.

A group of enzymes known as lysine methyl transferases and lysine demethylases are involved histone lysine modifications. One particular human lysine demethylase enzyme called Lysine Specific Demethylase-1 (LSD1) was recently discovered (Shi et al. (2004) *Cell* 119:941) and shown to be involved in histone lysine methylation. LSD1 has a fair degree of structural similarity, and amino acid identity/homology to polyamine oxidases and monoamine oxidases, all of which (i.e., MAO-A, MAO-B and LSD1) are flavin dependent amine oxidases which catalyze the oxidation of nitrogen-hydrogen bonds and/or nitrogen carbon bonds. Although the main target of LSD1 appears to be mono- and di-methylated histone lysines, specifically H3K4 and H3K9, there is evidence in the literature that LSD1 can demethylate methylated lysines on non-histone proteins like p53, E2F1, Dnmt1 and STAT3.

Several groups have reported LSD1 inhibitors in the literature. Sharma et al. recently reported a new series of urea and thiourea analogs based on an earlier series of polyamines which were shown to inhibit LSD1 and modulate histone methylation and gene expression in cells (J. Med. Chem. 2010 PMID: 20568780 [PubMed—as supplied by publisher]). Sharma et al. note that "To date, only a few existing compounds have been shown to inhibit LSD1." Some efforts were made to make analogs of the histone peptide that is methylated by the enzyme, other efforts have focused on more small molecule like molecules based on known MAO inhibitors. Gooden et al. reported trans-2-arylcyclopropylamine analogues that inhibit LSD1 with Ki values is the range of 188-566 micromolar (Gooden et al. ((2008) *Bioorg. Med. Chem. Let.* 18:3047-3051)). Most of these compounds were more potent against MAO-A as compared to MAO-B. Ueda et al. ((2009) J. Am. Chem. Soc. 131 (48): 17536-17537) reported cyclopropylamine analogs selective for LSD1 over MAO-A and MAO-B that were designed based on reported X-ray crystal structures of these enzymes with a phenylcyclopropylamine-FAD adduct and a FAD-N-propargyl lysine peptide. The reported IC50 values for phenylcyclopropylamine were about 32 micromolar for LSD1 whereas as compounds 1 and 2 had values of 2.5 and 1.9 micromolar respectively.

Importantly, studies have also been conducted on amine oxidase inhibitor compounds to determine selectivity for MAO-A versus MAO-B since MAO-A inhibitors can cause dangerous side-effects (see e.g., Yoshida et al. (2004) Bioorg. Med. Chem. 12(10):2645-2652; Hruschka et al. (2008) Biorg Med. Chem. (16):7148-7166; Folks et al. (1983) J. Clin. Psychopharmacol. (3)249; and Youdim et al. (1983) Mod. Probl. Pharmacopsychiatry (19):63).

Currently the treatments available for HBV and related diseases have serious drawbacks. There is a need for new drugs for these diseases that target novel points of intervention in the disease processes and avoid side-effects associated with certain targets.

Disclosure

The present invention relates to the treatment or prevention of Hepadnaviridae and diseases caused by such viruses, and in particular Hepatitis B. The inventors have unexpectedly found that inhibitors of LSD1 can reduce HBV DNA replication. This finding is unexpected since HBV replication goes through an RNA intermediate and the inventors are unaware of LSD1 being related to HBV. Advantageously, the use of selective LSD1 inhibitors or dual LSD1/MAOB inhibitors avoid side-effects associated with targets such as MAOA. The inventors found that administration of LSD1 inhibitors chronically was well tolerated in a mammal (and dual LSD1/MAOB inhibitors). Thus, the inventors have unexpectedly found that selective LSD1 inhibition or LSD1/MAOB dual inhibitions is a new therapeutic approach to treating and preventing Hepadnaviridae infection and related diseases and disorders.

The present invention provides for the treatment or prevention of Hepadnaviridae infection and disease caused by Hepadnaviridae infection. In particular, the invention provides compositions and methods that affect the ability of Hepadnaviridae to utilize the host's cellular machinery as part of the virus' lifecycle. The invention relates to the discovery that interfering with the normal ability of viruses to utilize the host cell machinery with LSD1 inhibitors reduces HBV replication. Thus, the treatment and prevention of Hepadnaviridae infection and disease caused by Hepadnaviridae according to the invention comprises administering to an individual in need of treatment, a therapeutically effective amount of a LSD1 inhibitor. The individual in need of treatment can be a human or, e.g., another mammal.

Accordingly, the invention provides HBV treatment or prevention methods or compositions based on inhibitors of LSD1.

In one embodiment, the invention provides a method of affecting the ability of HBV to replicate DNA. According to this method, an effective amount of a pharmaceutical composition comprising a LSD1 inhibitor is administered to an individual in need of treatment. The composition is preferably a small molecule inhibitor of LSD1.

In another embodiment, the invention provides a method of treating an individual infected with HBV by administering a therapeutically effective amount of a LSD1 inhibitor. According to one aspect of this embodiment, the LSD1 inhibitor is an irreversible or a reversible amine oxidase inhibitor. In one aspect, the irreversible amine oxidase inhibitor is a phenylcyclopropylamine derivative or analog, a phenelzine derivative or analog, or a propargylamine derivative or analog.

In yet another embodiment, the present invention provides a method of treating an individual infected with HBV by administering, to a patient in need of therapeutic or prophylactic treatment, an amount of a LSD1 inhibitor effective to reduce HBV DNA replication. Such treatments can be used to suppress the symptoms of HBV, i.e., suppressive therapy, or for treating episodic outbreaks, i.e., episodic therapy.

The invention further provides a method of identifying compounds that have HBV antiviral activity. More particularly, the method involves identifying compounds that inhibit LSD1 and then testing the LSD1 inhibitors in an HBV antiviral assay. According to this embodiment an assay system is employed to detect compounds and/or compositions that affect the ability of the virus to propagate itself.

In one aspect, the invention is a method of treating or preventing a symptom in an individual having infected with HBV comprising identifying a patient in need of such treatment and administering to said individual for a sufficient period of time an amount of a LSD1 inhibitor sufficient to improve symptom or reduce the rate of decline of the symptom thereby treating or preventing said symptom. In a related aspect, the invention is the use of a LSD1 inhibitor in an amount sufficient to modulate LSD1 activity for treating or preventing liver disease in an individual infected with HBV. In a specific aspect, the liver disease is liver cancer. In one embodiment of this aspect, the amount of LSD1 inhibitor administered is sufficient to modulate or inhibit LSD1 activity while not substantially inhibiting MAOA activity, thereby avoiding or reducing side-effects associated with administration of MAOA inhibitors.

In one aspect, the invention relates to a pharmaceutical composition for use in treating Hepadnaviridae comprising an anti-Hepadnaviridae effective amount of a LSD1 inhibitor.

In one aspect, the invention relates to a pharmaceutical composition for use in treating HBV infection comprising an anti-HBV effective amount of a LSD1 inhibitor.

In one aspect, the invention relates to a method of combination treatment. According to this method a LSD1 inhibitor and a second anti-HBV agent are administered to an individual in need of treatment. In one aspect, the second agent is chosen from an interferon agent or a DNA polymerase inhibitor.

In one aspect, the invention relates to a composition for combination treatment of HBV. Accordingly, the pharmaceutical composition of this aspect comprises a LSD1 inhibitor and a second anti-HBV agent along with a pharmaceutically acceptable carrier or excipient. In one aspect, the second agent is an interferon agent or an inhibitor of reverse transcriptase activity of the HBV DNA polymerase.

In one aspect, the second anti-HBV agent is Lamivudine, Adefovir Dipivoxil, Entecavir, Telbivudine, or Tenofovir.

In one aspect, the sufficient period of time for administering the LSD1 inhibitors is from 5 or more days to the individual, more preferably from 5 days to 4 years, even more preferably from 5 days to two years, yet even more preferably for 15 days to 2 years, and again yet even more preferably from 15 days to 1 year. In one aspect, the LSD1 inhibitor is administered daily in amount sufficient to yield a Cmax above the IC50 value for the LSD1 inhibitor.

Thus, the invention is as in any one of the following:

1) A method of for treating or preventing Hepadnaviridae infection or an associated disease or disorder comprising identifying an individual in need of such treatment and administering to said individual a LSD1 inhibitor.

2) The method as in 1, wherein said Hepadnaviridae infection is Hepatitis B virus.

3) The method as in 1, wherein said Hepadnaviridae infection is Hepatitis B virus resistance to one or more DNA polymerases inhibitors.

4) The method as in 1, wherein said LSD1 inhibitor is a reversible or irreversible amine oxidase inhibitor.

5) The method as in 1, wherein said LSD1 inhibitor inhibits Hepadnaviridae DNA replication.

6) The method as in 1, wherein said LSD1 inhibitor is a phenylcyclopropylamine derivative or homolog, a phenelzine homolog or derivative, or a propargylamine homolog or derivative.

7) The method as in 1, wherein said LSD1 has a therapeutic index of 10 or great.

8) The method as in 1, wherein said LSD1 has a therapeutic index of 20 or great.

9) The method as in 1, further comprising administering to said individual a second anti-HBV agent.

10) The method as in 9, wherein said second anti-HBV agent is an interferon agent or a DNA polymerase inhibitor.

11) A LSD1 inhibitor or a pharmaceutical composition comprising a LSD1 inhibitor for use in treating or preventing Hepadnaviridae infection or a related disease or disorder.

12) The LSD1 inhibitor as in 11, wherein said Hepadnaviridae infection is HBV infection.

13) A LSD1 inhibitor or a pharmaceutical composition comprising a LSD1 inhibitor and a second anti-HCV agent for use in treating or preventing Hepadnaviridae e infection or a related disease or disorder.

14) The LSD1 inhibitor as in 13, wherein said Hepadnaviridae infection is HBV infection.

15) The second anti-HBV agent as in 13 or 14, wherein said second anti-HBV an interferon agent or a DNA polymerase inhibitor.

16) The LSD1 inhibitor as in 11 to 15, wherein said LSD1 inhibitor is a reversible or irreversible amine oxidase inhibitor.

17) The LSD1 inhibitor as in 11 to 15, wherein said LSD1 inhibitor is an irreversible amine oxidase inhibitor.

18) The LSD1 inhibitor as in 11 to 15, wherein said LSD1 inhibitor is a phenylcyclopropylamine derivative or analog, a phenelzine derivative or analog, or a propargylamine derivative or analog.

19) The phenelzine derivative or analog as in 6 or 18, wherein said phenelzine analog or derivative:
  (a) has one, two, three, four or five substituents on the phenyl group;
  (b) has the phenyl group substituted with (exchanged for) an aryl or heterocyclyl group wherein said aryl or heterocyclyl group has zero, one, two, three, four or five substituents; or (c) as in (a) or (b) and having a substitution on the terminal nitrogen of the hydrazine group.

20) The propargylamine derivative or analog as in 6 or 18, wherein said propargylamine derivative or analog is a pargyline derivative or analog wherein:
  (a) said pargyline derivative or analog has one, two, three, four or five substituents on the phenyl group;
  (b) said pargyline derivative or analog has the phenyl group substituted with (exchanged for) an aryl or heterocyclyl group wherein said aryl or heterocyclyl group has zero, one, two, three, four or five substituents; or (c) as in (a) or (b) wherein the propargylmine moiety of pargyline has one or two substituents.

21) The phenylcyclopropylamine derivative or analog as in 6 or 18, wherein said phenylcyclopropylamine derivative or analog: (a) has one, two, three, four or five substituents on the phenyl group; or (b) the phenyl group substituted with (exchanged for) an aryl or heterocyclyl group wherein said aryl or heterocyclyl group has zero, one, two, three, four or five substituents; or (c) as in (a) or (b) and additionally having one or two substituents on the amino group of the cyclopropylamine core.

22) A method of treating HBV and HCV co-infection comprising identifying an individual in need of such treatment and administering to said individual a LSD1 inhibitor and optionally a second anti-HCV agent or anti-HBV agent.

23) The LSD1 inhibitor as in 1-21, wherein said LSD1 inhibitor has a therapeutic index of 10 or greater.

24) The phenylcyclopropylamine derivative or analog as in 6, 18, or 21, wherein the derivative or analog has the 1S,2R configuration in respect to the substituents on the cyclopropyl ring.

25) The phenylcyclopropylamine derivative or analog as in 6, 18, or 21, wherein the derivative or analog has the 1R,2S configuration in respect to the substituents on the cyclopropyl ring.

BRIEF DESCRIPTION OF THE DRAWINGS

FIG. 1 summarizes structure-activity relationship evolution of increased potency towards LSD1 as compared to MAOA and/or MAOB from compounds that were not selective (e.g., tranylcypromine) to compounds that are selective inhibitors of LSD1 with IC50 values in the low nanomolar range.

FIG. 2 summarizes structure-activity relationship evolution of increased potency towards LSD1 and MAOB as compared to MAOA from compounds that were not selective for LSD1 and MAOB (e.g., tranylcypromine). The dual LSD1/MAOB compounds have IC50 values for these two targets in the low nanomolar range.

FIG. 3 shows the results of a western blot stained for H3K4 methylation with SH-SY5Y cells grown in the presence of Compound Dual-1 or parnate for 1, 2, and 3 days, showing that this compound reduces H3K4 methylation in cells in a time dependent manner. Each triplet of bars in the graph represent from left to right (1) vehicle treated cells, (2) cells treated with 1 uM Compound Dual-1, and (3) cells treated with 5 uM Dual-1.

DETAILED DESCRIPTION OF THE INVENTION

The inventors have unexpectedly found that inhibitors of LSD1 can reduce HBV DNA replication. This finding is unexpected since HBV is thought to go through an RNA replicative intermediate and the most well characterized functions of LSD1 relate to histone methylation and its effect on modulating DNA transcription and the inventors are not aware of any reports of LSD1 being associated with HBV. Thus, the inventors have shown that LSD1 inhibitors inhibit the ability of DNA viruses such as HBV, a member of the Hepadnaviridae family of viruses. This finding is significant since HBV can mutate and develop resistance to therapeutics targeted to viral proteins. Thus, the methods and compositions of the invention can be useful for treating viruses and viral infections resistant to current treatments or treatment that are in developments and eventually clinically approved. Additionally, the methods and compositions of the invention can be useful for treating viruses or viral infection while reducing the likelihood of the virus or viral infection to developing resistance to current treatments or treatment that are in developments and eventually clinically approved. Other advantages are and more details of the invention are described in more detail below.

Figure 1:
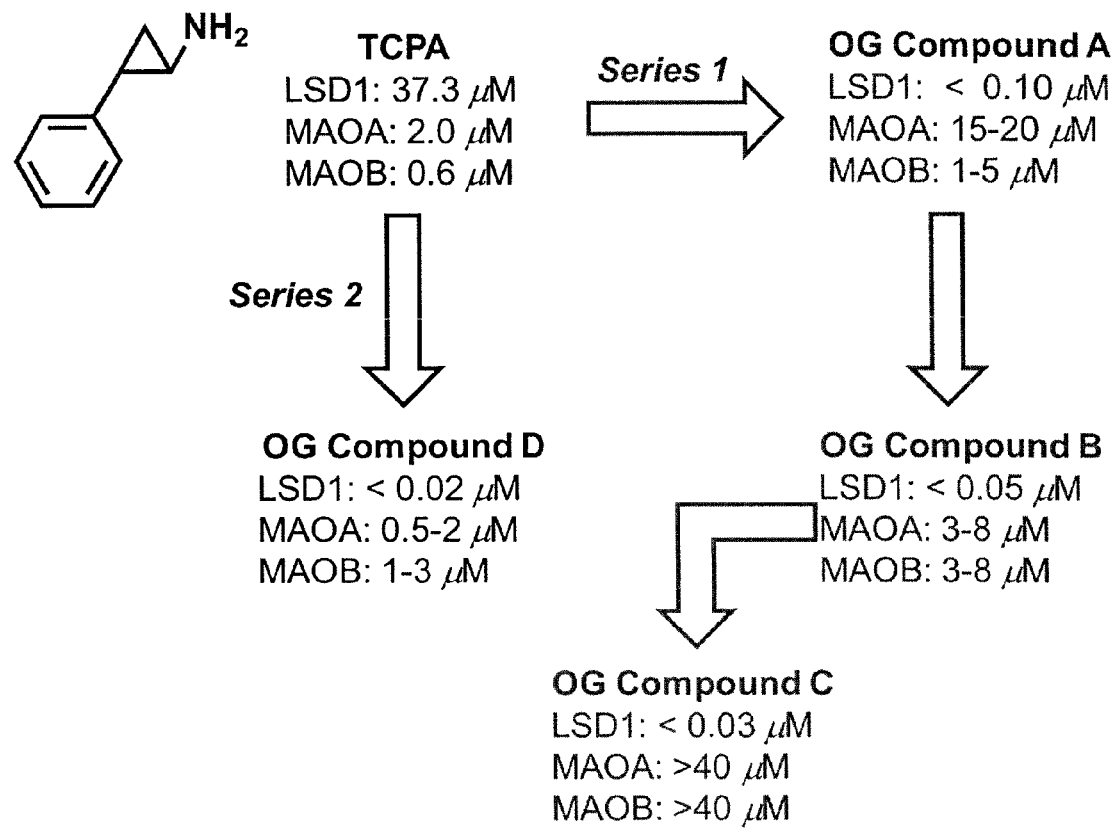
FIG. 1 Optimization of Selective LSD1 Inhibitors.
Figure 2:
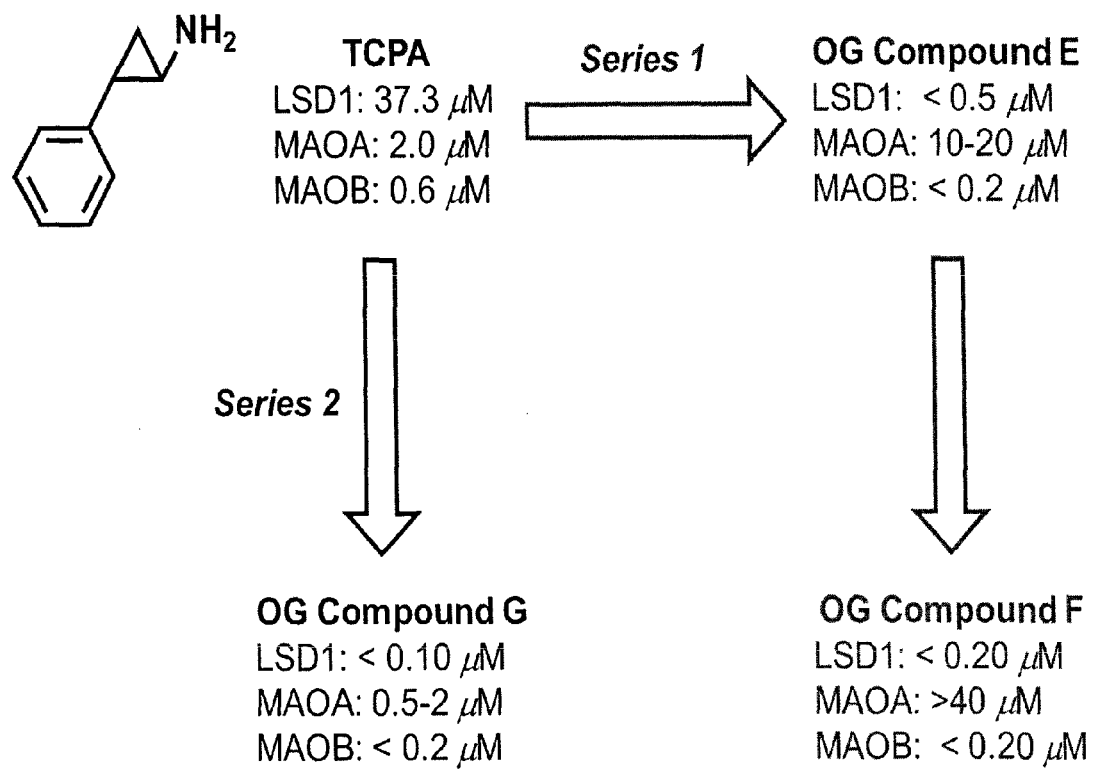
FIG. 2 Optimization of Dual LSD1/MAOB Inhibitors.
Figure 3A:
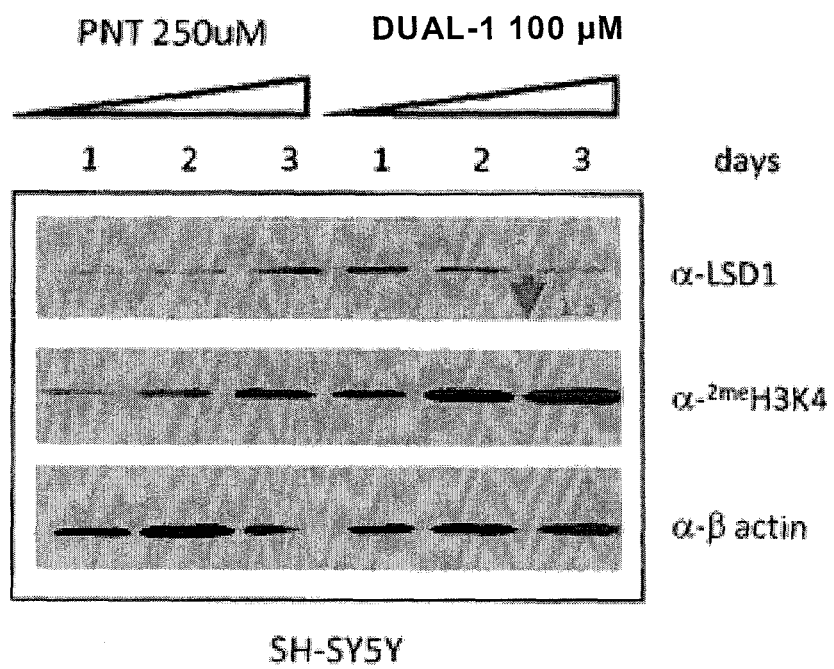
FIG. 3 (constituted by FIG. 3A and FIG. 3B) Compound Dual-1 Increases Histone Methylation.
Figure 3B:
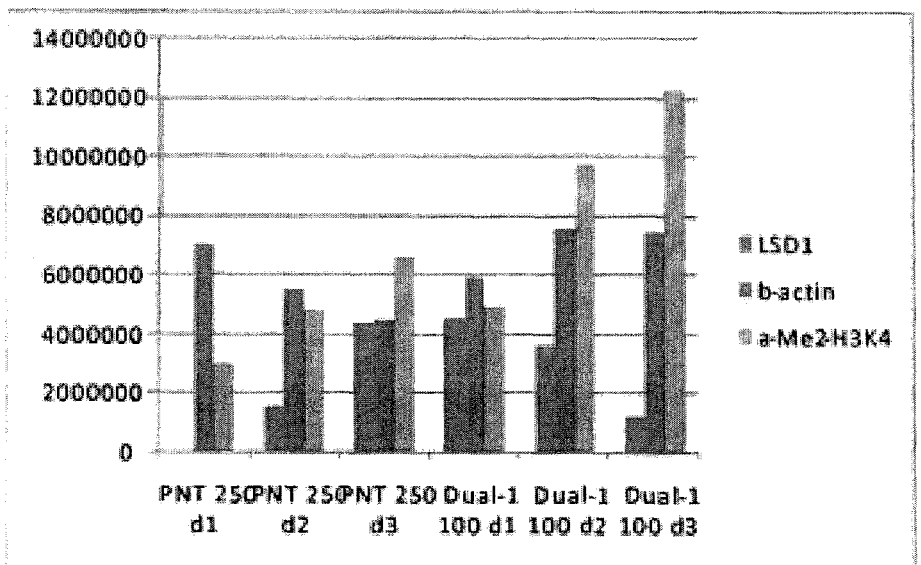

A medicinal chemistry effort undertaken by some of the inventors resulted in the synthesis and identification of small molecule, potent selective LSD1 inhibitors and potent dual inhibitors of LSD1 and MAOB. This effort resulted in the identification of a number of compounds having different selectivities for LSD1, MAOA, and MAOB. See FIG. 1.

Subsequent studies of some of the optimized compounds with a neural derived cell line and other cell lines indicted that both selective LSD1 inhibitors and dual inhibitors of LSD1 and MAOB can increase histone methylation levels at the cellular level indicating that these compounds inhibit cellular lysine demethylase activity. Furthermore, these LSD1 inhibitors show dose dependent effects on gene expression levels in these cells.

Lastly the LSD1 inhibitors were to be able to be administered to mammals chronically at doses that are thought to achieve levels of the inhibitor sufficient for causing a biological effect.

As a result of these studies, Compound X, a potent LSD1 inhibitor, was shown to have activity in the low micromolar range in an HBV DNA replication assay. Without wishing to be bound by theory, it is believed that other LSD1 inhibitors inhibit HBV DNA replication and have use for treating or preventing Hepadnaviridae infection or an associated disease or disorder. More specifically, it is believed that LSD1 inhibitors, as a result of this invention, have use in treating or prevent HBV or an associated disease or disorder.

Methods of Treatment or Prevention and Disease

The invention relates to methods of treatment or prevention of diseases or disorders related to Hepadnaviridae infection.

In one embodiment, the invention is the use of a LSD1 inhibitor for treating or preventing Hepadnaviridae infection. In a related aspect, the invention is a method treating or preventing Hepadnaviridae infection comprising administering a LSD1 inhibitor to an individual. In another related aspect, the invention is a method treating or preventing Hepadnaviridae infection comprising administering a LSD1 inhibitor to an individual in need of such treatment. In yet another related aspect, the invention is a method treating or preventing Hepadnaviridae infection comprising identifying an individual in need of such treatment or prevention and administering a LSD1 inhibitor to said individual. In one aspect, the LSD1 inhibitor is a selective inhibitor of LSD1. In one aspect, the LSD1 inhibitor is a selective inhibitor of LSD1 and MAOB. In one aspect, the LSD1 inhibitor is an irreversible or a reversible amine oxidase inhibitor. In one aspect, the irreversible amine oxidase inhibitor is a phenylcyclopropylamine derivative or analog, a phenelzine derivative or analog, or a propargylamine derivative or analog. In one aspect of this embodiment, the LSD1 inhibitor has a therapeutic index of 5 or greater. In one aspect of this embodiment, the LSD1 inhibitor has a therapeutic index of 10 or greater. In one aspect of this embodiment, the LSD1 inhibitor has a therapeutic index of 100 or greater.

In one embodiment, the invention is the use of a LSD1 inhibitor for inhibiting Hepadnaviridae DNA replication. In a related aspect, the invention is a method inhibiting Hepadnaviridae DNA replication comprising administering a LSD1 inhibitor to an individual. In another related aspect, the invention is a method of inhibiting Hepadnaviridae DNA replication comprising administering a LSD1 inhibitor to an individual in need of such treatment. In yet another related aspect, the invention is a method of inhibiting Hepadnaviridae DNA replication comprising identifying an individual in need of such treatment or prevention and administering a LSD1 inhibitor to said individual. In one aspect, the LSD1 inhibitor is a selective inhibitor of LSD1. In one aspect, the LSD1 inhibitor is a selective inhibitor of LSD1 and MAOB. In one aspect, the LSD1 inhibitor is an irreversible or a reversible amine oxidase inhibitor. In one aspect, the irreversible amine oxidase inhibitor is a phenylcyclopropylamine derivative or analog, a phenelzine derivative or analog, or a propargylamine derivative or analog. In one aspect of this embodiment, the LSD1 inhibitor has a therapeutic index of 5 or greater. In one aspect of this embodiment, the LSD1 inhibitor has a therapeutic index of 10 or greater. In one aspect of this embodiment, the LSD1 inhibitor has a therapeutic index of 100 or greater. In one aspect of this embodiment, the Hepadnaviridae is HBV.

In one embodiment, the invention is the use of a LSD1 inhibitor for treating or preventing HBV infection. In a related aspect, the invention is a method treating or preventing HBV infection comprising administering a LSD1 inhibitor to an individual. In another related aspect, the invention is a method treating or preventing HBV infection comprising administering a LSD1 inhibitor to an individual in need of such treatment. In yet another related aspect, the invention is a method treating or preventing HBV infection comprising identifying an individual in need of such treatment or prevention and administering a LSD1 inhibitor to said individual. In one aspect, the LSD1 inhibitor is a selective inhibitor of LSD1. In one aspect, the LSD1 inhibitor is a selective inhibitor of LSD1 and MAOB. In one aspect, the LSD1 inhibitor is an irreversible or a reversible amine oxidase inhibitor. In one aspect, the irreversible amine oxidase inhibitor is a phenylcyclopropylamine derivative or analog, a phenelzine derivative or analog, or a propargylamine derivative or analog. In one aspect of this embodiment, the LSD1 inhibitor has a therapeutic index of 5 or greater. In one aspect of this embodiment, the LSD1 inhibitor has a therapeutic index of 10 or greater. In one aspect of this embodiment, the LSD1 inhibitor has a therapeutic index of 100 or greater.

In one embodiment, the invention is the use of a LSD1 inhibitor for inhibiting HBV DNA replication. In a related aspect, the invention is a method inhibiting HBV DNA replication comprising administering a LSD1 inhibitor to an individual. In another related aspect, the invention is a method of inhibiting HBV DNA replication comprising administering a LSD1 inhibitor to an individual in need of such treatment. In yet another related aspect, the invention is a method of inhibiting HBV DNA replication comprising identifying an individual in need of such treatment or prevention and administering a LSD1 inhibitor to said individual. In one aspect, the LSD1 inhibitor is a selective inhibitor of LSD1. In one aspect, the LSD1 inhibitor is a selective inhibitor of LSD1 and MAOB. In one aspect, the LSD1 inhibitor is an irreversible or a reversible amine oxidase inhibitor. In one aspect, the irreversible amine oxidase inhibitor is a phenylcyclopropylamine derivative or analog, a phenelzine derivative or analog, or a propargylamine derivative or analog. In one aspect of this embodiment, the LSD1 inhibitor has a therapeutic index of 5 or greater. In one aspect of this embodiment, the LSD1 inhibitor has a therapeutic index of 10 or greater. In one aspect of this embodiment, the LSD1 inhibitor has a therapeutic index of 100 or greater.

The patient, subject, or individual, such as the individual in need of treatment or prevention, may be, e.g., a eukaryote, an animal, a vertebrate animal, a mammal, a rodent (e.g., a guinea pig, a hamster, a rat, a mouse), a murine (e.g., a mouse), a canine (e.g., a dog), a feline (e.g., a cat), an equine (e.g., a horse), a primate, a simian (e.g., a monkey or ape), a monkey (e.g., a marmoset, a baboon), an ape (e.g., gorilla, chimpanzee, orangutan, gibbon), or a human. The meaning of the terms "eukaryote," "animal," "mammal," etc., is well known in the art and can, for example, be deduced from Wehner and Gehring (1995; Thieme Verlag). In the context of this invention, it is particularly envisaged that animals are to be treated which are economically, agronomically or scientifically important. Scientifically important organisms include, but are not limited to, mice, rats, rabbits, fruit flies like *Drosophila melagonaster* and nematodes like *Caenorhabditis elegans*. Non-limiting examples of agronomically important animals are sheep, cattle and pig, while, for example, cats and dogs may be considered as economically important animals. Preferably, the subject/patient is a mammal; more preferably, the subject/patient is a human.

As used herein, the term "treating a disease or disorder" refers to a slowing of or a reversal of the progress of the disease. Treating a disease or disorder includes treating a symptom and/or reducing the symptoms of the disease.

As used herein, the term "preventing a disease or disorder" refers to a slowing of the disease or of the onset of the disease or the symptoms thereof. Preventing a disease or disorder can include stopping the onset of the disease or symptoms thereof.

In another aspect, the invention is a method of treating HBV comprising identifying an individual in need of such treatment and administering to said individual for a sufficient period of time an amount of a LSD1 inhibitor sufficient to treat or prevent HBV. In a related aspect, the invention is the use of a LSD1 inhibitor in an amount sufficient to modulate LSD1 activity for treating or preventing HBV. In a specific aspect, said treatment reduces HBV DNA replication. In one embodiment of this aspect, the amount of selective LSD1 inhibitor administered is sufficient to modulate or inhibit LSD1 activity while not substantially inhibiting MAOA activity, thereby avoiding or reducing side-effects associated with administration of MAOA inhibitors. In a specific aspect of this embodiment, preferably the amount of LSD1 inhibitor administered per day to a human is from about 0.5 mg to about 500 mg per day. More preferably the amount of LSD1 inhibitor administered per day to a human is from about 0.5 mg to about 200 mg per day or is a pharmaceutical composition formulated in such a way as to deliver this amount of free base equivalent (or free acid equivalent depending on the parent molecule). Preferably, the LSD1 inhibitor is administered or formulated to be administered for 5 or more days to the individual, more preferably from 5 days to 4 years, even more preferably from 5 days to two years, yet even more preferably for 15 days to 2 years, and again yet even more preferably from 15 days to 1 year. It is noted that in this context administration for, e.g., 5 or more days, means an amount sufficient over a time sufficient to cause pharmacologic inhibition of LSD1 over this period of time and this does not necessarily mean administration of compound every day or only once per day. Depending on the PK/ADME properties of the inhibitors, a suitable amount and dosing regimen can be determined by a skilled practitioner in view of this disclosure.

In one aspect, the invention is a method of treating or preventing HBV comprising identifying an individual in need of such treatment and administering to said individual for a sufficient period of time an amount of a dual LSD1/MAOB inhibitor sufficient to treat or prevent HBV. In a related aspect, the invention is the use of a dual LSD1/MAOB inhibitor in an amount sufficient to modulate LSD1 activity for treating or preventing HBV. In a specific aspect, treating or preventing HBV comprises inhibiting HBV DNA replication. In one embodiment of this aspect, the amount of selective LSD1 inhibitor administered is sufficient to modulate or inhibit LSD1 and MAOB activity while not substantially inhibiting MAOA activity, thereby avoiding or reducing side-effects associated with administration of MAOA inhibitors. In a specific aspect of this embodiment, preferably the amount of LSD1/MAOB inhibitor administered per day to a human is from about 0.5 mg to about 500 mg per day. More preferably the amount of LSD1/MAOB inhibitor administered per day to a human is from about 0.5 mg to about 200 mg per day or is a pharmaceutical composition formulated in such a way as to deliver this amount of free base equivalent (or free acid equivalent depending on the parent molecule). In one embodiment of this aspect, the amount of LSD1/MAOB inhibitor administered is sufficient to modulate or inhibit LSD1/MAOB activity while not substantially inhibiting MAO-A activity, thereby avoiding or reducing side-effects associated with administration of MAO-A inhibitors. Preferably, the dual LSD1/MAOB inhibitor is administered or formulated to be administered for 5 or more days to the individual, more preferably from 5 days to 4 years, even more preferably from 5 days to two years, yet even more preferably for 15 days to 2 years, and again yet even more preferably from 15 days to 1 year. It is noted that in this context administration for, e.g., 5 or more days, means an amount sufficient over a time sufficient to cause pharmacologic inhibition of LSD1 and MAOB over this period of time and this does not necessarily mean administration of compound every day or only once per day. Depending on the PK/ADME properties of the inhibitors, a suitable amount and dosing regimen can be determined by a skilled practitioner in view of this disclosure.

In one aspect, the invention is a method of treating or preventing HBV comprising identifying an individual in need of such treatment and administering to said individual for a sufficient period of time an amount of a LSD1 inhibitor and an interferon agent sufficient to treat or prevent HBV. In a related aspect, the invention is the use of a LSD1 inhibitor and an interferon agent in an amount sufficient for treating or preventing HBV. In a specific aspect, treating or preventing HBV comprises inhibiting HBV DNA replication via LSD1 and inhibiting HBV via an interferon dependent mechanism. In one embodiment of this aspect, the amount of interferon administered avoids or reduces side-effects associated with administration of higher doses of interferon. In a specific aspect of this embodiment, preferably the amount of LSD1 administered per day to a human is from about 0.5 mg to about 500 mg per day. More preferably the amount of LSD1 inhibitor administered per day to a human is from about 0.5 mg to about 200 mg per day or is a pharmaceutical composition formulated in such a way as to deliver this amount of free base equivalent (or free acid equivalent depending on the parent molecule). In one embodiment of this aspect, the amount of the interferon agent administered to the individual is sufficient to treat or prevent HBV. More preferably, the amount of the interferon agent administered to the individual is sufficient to treat or prevent HBV while avoiding or lessening the side effects associated with higher doses of an interferon agent. Depending on the PK/ADME properties of the inhibitors and interferon agent a suitable amount and dosing regimen can be determined by a skilled practitioner in view of this disclosure.

In one aspect, the invention is a method of treating or preventing HBV comprising identifying a individual in need of such treatment and administering to said individual for a sufficient period of time an amount of a LSD1 inhibitor and a second anti-HBV agent sufficient to treat or prevent HBV. In a related aspect, the invention is the use of a LSD1 inhibitor and a second anti-HBV agent in an amount sufficient for treating or preventing HBV. In a specific aspect, treating or preventing HBV comprises inhibiting HBV DNA replication via LSD1 and inhibiting HBV with a HBV DNA polymerase inhibitor (reverse transcriptase). In one aspect, the second anti-HBV agent is chosen from Lamivudine, Adefovir Dipivoxil, Entecavir, Telbivudine, or Tenofovir. In one embodiment of this aspect, the amount of second anti-HBV agent is sufficient to prevent or treat HBV. In one embodiment of this aspect, the amount of second anti-HBV agent administered is sufficient to prevent or treat HBV while avoiding or reducing side-effects associated with administration of higher doses of second anti-HBV agent. In one aspect, the second anti-HBV agent is Lamivudine, Adefovir Dipivoxil, Entecavir, Telbivudine, or Tenofovir. In one aspect, the second anti-HBV agent is an interferon agent. In a specific aspect of this embodiment, preferably the amount of LSD1 administered per day to a human is from about 0.5 mg to about 500 mg per day. More preferably the amount of LSD1 inhibitor administered per day to a human is from about 0.5 mg to about 200 mg per day or is a pharmaceutical composition formulated in such a way as to deliver this amount of free base equivalent (or free acid equivalent depending on the parent molecule). In one embodiment of this aspect, the amount of the second anti-HBV agent administered to the individual is from 0.050 to 1000 mg daily. More preferably, the amount of the second anti-HBV agent is administered to the individual is from 0.050 to 500 mg daily. Even more preferably, the amount of the second anti-HBV agent administered to the individual is from 0.050 to 200 mg daily. Depending on the PK/ADME properties of the inhibitors, a suitable amount and dosing regimen can be determined by a skilled practitioner in view of this disclosure.

In one aspect, the invention relates to treating or preventing a disease or disorder associated with co-infection of HBV and HCV comprising identifying a patient co-infected or suspected of being co-infected with HBV and HCV and administering to said patient a therapeutically effective amount of an LSD1 inhibitor and one or more anti-HCV or anti-HBV agents. One preferred anti-HCV or anti-HBV agent is an interferon agent. Other anti-HBV agents include In one aspect, the second anti-HBV agent is Lamivudine, Adefovir Dipivoxil, Entecavir, Telbivudine, or Tenofovir. Other anti-HCV agents include protease inhibitors, nucleoside polymerase inhibitors, non-nucleoside polymerase inhibitors, and NS5A inhibitors. Unexpectedly, as described in a co-filed application entitled "LYSINE DEMETHYLASE INHIBITORS FOR DISEASES AND DISORDERS ASSOCIATED WITH FLAVIVIRIDAE" under Oryzon Docet No. 3020-P, the inventors have found that LSD1 inhibitors reduce HCV RNA replication. While not wishing to be bound by theory, it is believed that treatment of HCV and HBV co-infection with an LSD1 inhibitor according to the invention yields unexpected benefits.

Compounds, Formulation, and Routes of Administration

The selective LSD1 inhibitors and dual LSD1/MAOB inhibitors for use in the invention can be synthesized by a number of techniques.

Examples of selective LSD1 and LSD1/MAOB dual inhibitors are given in, e.g., WO2010/043721 (PCT/EP2009/063685), WO2010/084160 (PCT/EP2010/050697), PCT/EP2010/055131; PCT/EP2010/055103; and EP application number EP10171345 all of which are explicitly incorporated herein by reference in their entireties to the extent they are not inconsistent with the instant disclosure.

In one specific aspect, a phenylcyclopropylamine derivative or homolog for use in the invention is phenylcyclopropylamine with one or two substitutions on the amine group; phenylcyclopropylamine with zero, one or two substitutions on the amine group and one, two, three, four, or five substitution on the phenyl group; phenylcyclopropylamine with one, two, three, four, or five substitution on the phenyl group; phenylcyclopropylamine with zero, one or two substitutions on the amine group wherein the phenyl group of PCPA is substituted with (exchanged for) another ring system chosen from aryl or heterocyclyl to give an aryl- or heteroaryl-cyclopropylamine having zero, one or two substituents on the amine group; phenylcyclopropylamine wherein the phenyl group of PCPA is substituted with (exchanged for) another ring system chosen from aryl or heterocyclyl to give an aryl- or heterocycyl-cyclopropylamine wherein said aryl- or heterocyclyl-cyclopropylamine on said aryl or heterocyclyl moiety has zero, one or two substitutions on the amine group and one, two, three, four, or five substitution on the phenyl group; phenylcyclopropylamine with one, two, three, four, or five substitution on the phenyl group; or any of the above described phenylcyclopropylamine analogs or derivatives wherein the cyclopropyl has one, two, three or four additional substituents. Preferably, the heterocyclyl group described above in this paragraph in a heteroaryl.

Examples of phenylcyclopropylamine derivatives or analogs are for example "cyclopropylamine amide" derivatives and "cyclopropylamine" derivatives as defined herein.

Specific examples of "cyclopropylamine acetamide" derivatives include, but are not limited to:
N-cyclopropyl-2-{[(trans)-2-phenylcyclopropyl] amino}acetamide;
2-{[(trans)-2-phenylcyclopropyl]amino}acetamide;
N-cyclopropyl-2-{[(trans)-2-phenylcyclopropyl] amino}propanamide;
2-{[(trans)-2-phenylcyclopropyl]amino}-N-prop-2-ynylacetamide;
N-isopropyl-2-{[(trans)-2-phenylcyclopropyl] amino}acetamide;
N-(tert-butyl)-2-{[(trans)-2-phenylcyclopropyl] amino}acetamide;
N-(2-morpholin-4-yl-2-oxoethyl)-N-[(trans)-2-phenylcyclopropyl]amine;
2-{[(trans)-2-phenylcyclopropyl]amino}propanamide;
Methyl 2-{[(trans)-2-phenylcyclopropyl]amino}propanoate;
1-(4-methylpiperazin-1-yl)-2-((trans)-2-phenylcyclopropylamino)ethanone;
1-(4-ethylpiperazin-1-yl)-2-((trans)-2-phenylcyclopropylamino)ethanone;
1-(4-benzylpiperazin-1-yl)-2-((trans)-2-phenylcyclopropylamino)ethanone;
2-((trans)-2-phenylcyclopropylamino)-1-(4-phenylpiperazin-1-yl)ethanone;
2-((trans)-2-(4-(benzyloxy)phenyl)cyclopropylamino)-1-(4-methylpiperazin-1-yl)ethanone;
2-((trans)-2-(1,1'-biphenyl-4-yl)cyclopropylamino)-1-(4-methylpiperazin-1-yl)ethanone;
2-((trans)-2-(4-(benzyloxy)phenyl)cyclopropylamino)-N-cyclopropylacetamide;
2-((trans)-2-(4-(3-fluorobenzyloxy)phenyl)cyclopropylamino)-1-(4-methylpiperazin-1-yl)ethanone;
2-((trans)-2-(4-(4-fluorobenzyloxy)phenyl)cyclopropylamino)-1-(4-methylpiperazin-1-yl)ethanone;
2-((trans)-2-(4-(3-chlorobenzyloxy)phenyl)cyclopropylamino)-1-(4-methylpiperazin-1-yl)ethanone;
1-(4-methylpiperazin-1-yl)-2-((trans)-2-(4-phenethoxyphenyl)cyclopropylamino)ethanone;
2-((trans)-2-(biphenyl-4-yl)cyclopropylamino)-1-(4-methylpiperazin-1-yl)ethanone; N-cyclopropyl-2-{[(trans)-2-phenylcyclopropyl]amino}acetamide;
N-methyl-trans-2-(Phenylcyclopropylamino)propanamide;
2-{methyl[(trans)-2-phenylcyclopropyl]amino}acetamide;
N-[2-(4-methylpiperazin-1-yl)ethyl]-N-[(trans)-2-phenylcyclopropyl]amine;
N-cyclopropyl-N'-[(trans)-2-phenylcyclopropyl]ethane-1,2-diamine;

N,N-dimethyl-N'-(2-{[(trans)-2-phenylcyclopropyl]amino}ethyl)ethane-1,2-diamine;
(3R)-1-(2-{[(trans)-2-phenylcyclopropyl]amino}ethyl)pyrrolidin-3-amine;
(3S)—N,N-dimethyl-1-(2-{[(trans)-2-phenylcyclopropyl]amino}ethyl) pyrrolidin-3-amine;
(3R)—N,N-dimethyl-1-(2-{[(trans)-2-phenylcyclopropyl]amino}ethyl) pyrrolidin-3-amine;
N-[(trans)-2-phenylcyclopropyl]-N-(2-piperazin-1-ylethyl)amine;
N,N-diethyl-N'-[(trans)-2-phenylcyclopropyl]ethane-1,2-diamine;
N-[(trans)-2-phenylcyclopropyl]-N-(2-piperidin-1-ylethyl)amine;
(trans)-2-(4-(benzyloxy)phenyl)-N-(2-(4-methylpiperazin-1-yl)ethyl)cyclopropanamine;
(trans)-N-(2-(4-methylpiperazin-1-yl)ethyl)-2-(3'-(trifluoromethyl)biphenyl-4-yl)cyclopropanamine;
(trans)-2-(3'-chlorobiphenyl-4-yl)-N-(2-(4-methylpiperazin-1-yl)ethyl)cyclopropanamine;
(R)-1-(2-((trans)-2-(3'-(trifluoromethyl)biphenyl-4-yl)cyclopropylamino) ethyl)pyrrolidin-3-amine; and
$N^1$-cyclopropyl-$N^2$-((trans)-2-(3'-(trifluoromethyl)biphenyl-4-yl)cyclopropyl)ethane-1,2-diamine.

Specific examples of "cyclopropylamine" derivatives, include, but are not limited to:
N-4-fluorobenzyl-N-{(trans)-2-[4-(benzyloxy)phenyl]cyclopropyl}amine,
N-4-methoxybenzyl-N-{(trans)-2-[4-(benzyloxy)phenyl]cyclopropyl}amine,
N-benzyl-N-{(trans)-2-[4-(benzyloxy)phenyl]cyclopropyl}amine,
N-[(trans)-2-phenylcyclopropyl]amino-methyl)pyridin-3-ol,
N-[(trans)-2-phenylcyclopropyl]-N-(3-methylpyridin-2-ylmethyl)amine,
N-[(trans)-2-phenylcyclopropyl]-N-(4-chloropyridin-3-ylmethyl)amine,
N-[(trans)-2-phenylcyclopropyl]-N-(4-trifluoromethylpyridin-3-ylmethyl)amine,
N-(3-methoxybenzyl)-N-[(trans)-2-phenylcyclopropyl]amine,
N-[(trans)-2-phenylcyclopropyl]-N-(quinolin-4-ylmethyl)amine,
N-(2-fluorobenzyl)-N-[(trans)-2-phenylcyclopropyl]amine,
N-(3-fluorobenzyl)-N-[(trans)-2-phenylcyclopropyl]amine,
N-[(trans)-2-phenylcyclopropyl]-N-(3,4-dichloro-1-phenylmethyl)amine,
N-[(trans)-2-phenylcyclopropyl]-N-(5-bromo-thiophen-2-ylmethyl)amine,
N-[(trans)-2-phenylcyclopropyl]-N-(3-bromo-thiophen-2-ylmethyl)amine,
N-[(trans)-2-phenylcyclopropyl]-N-(thiophen-2-ylmethyl)amine,
N-[(trans)-2-phenylcyclopropyl]-N-(1,3-thiazol-2-ylmethyl)amine,
N-[(trans)-2-phenylcyclopropyl]-N-(3-methyl-pyridin-2-ylmethyl)amine,
N-[(trans)-2-phenylcyclopropyl]-N-(pyridin-4-ylmethyl)amine,
N-[(trans)-2-phenylcyclopropyl]-N-(pyridin-3-ylmethyl)amine,
N-[(trans)-2-phenylcyclopropyl]-N-(pyridin-2-ylmethyl)amine,
[(trans)-2-phenylcyclopropyl]-N-[4-(trifluoromethyl)benzyl]amine,
({[(trans)-2-phenylcyclopropyl]amino}methyl)benzonitrile,
N-(4-fluorobenzyl)-N-[(trans)-2-phenylcyclopropyl]amine,
N-[(trans)-2-phenylcyclopropyl]-N-(3-bromo-pyridin-2-ylmethyl)amine,
N-4-cyanobenzyl-N-{(trans)-2-[4-(benzyloxy)phenyl]cyclopropyl}amine,
N-4-[(benzyloxy)-benzyl]-N-[(trans)-2-(4-phenyl)cyclopropyl]amine;
2-((trans)-2-(4-(4-cyanobenzyloxy)phenyl)cyclopropylamino)acetamide,
2-((trans)-2-(4-(3-cyanobenzyloxy)phenyl)cyclopropylamino)acetamide,
2-((trans)-2-(4-(benzyloxy)phenyl)cyclopropylamino)acetamide,
2-((trans)-2-(4-(4-fluorobenzyloxy)phenyl)cyclopropylamino)acetamide,
2-((trans)-2-(4-(3-fluorobenzyloxy)phenyl)cyclopropylamino)acetamide,
2-((trans)-2-(4-(3-chlorobenzyloxy)phenyl)cyclopropylamino)acetamide,
2-((trans)-2-(4-(4-chlorobenzyloxy)phenyl)cyclopropylamino)acetamide,
2-((trans)-2-(4-(3-bromobenzyloxy)phenyl)cyclopropylamino)acetamide,
2-((trans)-2-(4-(3,5-difluorobenzyloxy)phenyl)cyclopropylamino)acetamide,
2-((trans)-2-(4-phenethoxyphenyl)cyclopropylamino)acetamide,
2-((trans)-2-(3'-(trifluoromethyl)biphenyl-4-yl)cyclopropylamino) acetamide, and 2-((trans)-2-(3'-chlorobiphenyl-4-yl)cyclopropylamino)acetamide.

Other examples of LSD1 inhibitors are, e.g., phenelzine or pargyline (propargylamine) or a derivative or analog thereof. Derivatives and analogs of phenelzine and pargyline (propargylamine) include, but are not limited to, compounds where the phenyl group of the parent compound is replaced with a heteroaryl or optionally substituted cyclic group or the phenyl group of the parent compound is optionally substituted with a cyclic group. In one aspect, the phenelzine or pargyline derivative or analog thereof has selective LSD1 or dual LSD1/MAOB inhibitory activity as described herein. In one aspect, the phenelzine derivative or analog has one, two, three, four or five substituents on the phenyl group. In one aspect, the phenelzine derivative or analog has the phenyl group substituted with (exchanged for) an aryl or heterocyclyl group wherein said aryl or heterocyclyl group has zero, one, two, three, four or five substituents. In one aspect, the pargyline derivative or analog has one, two, three, four or five substituents on the phenyl group. In one aspect, the pargyline derivative or analog has the phenyl group substituted with (exchanged for) an aryl or heterocyclyl group wherein said aryl or heterocyclyl group has zero, one, two, three, four or five substituents. Methods of preparing such compounds are known to the skilled artisan.

As used herein, the term "aryl," refers a carbocyclic aromatic system containing one ring, or two or three rings fused together where in the ring atoms are all carbon. The term "aryl" groups includes, but is not limited to groups such as phenyl, naphthyl, or anthracenyl.

As used herein, the term "heterocyclyl" or "heterocycle," each refer to a saturated, partially unsaturated, or fully unsaturated monocyclic, bicyclic, or tricyclic heterocyclic group containing at least one heteroatom as a ring member, wherein each said heteroatom may be independently selected from the group consisting of nitrogen, oxygen, and sulfur wherein the nitrogen or sulfur atoms may be oxidized (e.g., —N=O, —S(=O)—, or —S(=O)$_2$—). Additionally, 1, 2, or 3 of the carbon atoms of the heterocyclyl may be optionally oxidized (e.g., to give an oxo group or =O). One group of heterocyclyls has from 1 to 4 heteroatoms as ring members. Another group of heterocyclyls has from 1 to 2 heteroatoms as ring members. One group of heterocyclyls has from 3 to 8 ring members in each ring. Yet another group of heterocyclyls has from 3 to 7 ring members in each ring. Again another group of heterocyclyls has from 5 to 6 ring members in each ring. "Heterocyclyl" is intended to encompass a heterocyclyl group fused to a carbocyclyl or benzo ring systems. Examples of heterocyclyl groups include, but are not limited to, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, or imidazolidinyl. Examples of heteroaryls that are heterocyclyls include, but are not limited to, pyridinyl, imidazolyl, imidazopyridinyl, pyrimidinyl, pyrazolyl, triazolyl, pyrazinyl, tetrazolyl, furyl, thienyl, isoxazolyl, thiazolyl, oxadiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, or furopyridinyl.

As used herein, the term "heteroaryl," refers to a 3 to 7 membered unsaturated monocyclic ring, or a fused monocyclic, bicyclic, or tricyclic ring system in which the rings are aromatic and which at least one ring contains at least one atom selected from the group consisting of O, S, and N. One group of heteroaryls has from 5 to 7 carbon atoms. Examples of heteroaryl groups include, but are not limited to, pyridinyl, imidazolyl, imidazopyridinyl, pyrimidinyl, pyrazolyl, triazolyl, pyrazinyl, tetrazolyl, furyl, thienyl, isoxazolyl, thiazolyl, oxadiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, or furopyridinyl.

In reference to the substituents referred to above, as the skilled artisan is aware, the appropriate selection of the substituents can be made in view of the disclosure herein to provide LSD1 inhibitors, selective LSD1 inhibitors, and dual LSD1/MAOB inhibitors for use in the methods and compositions of the invention.

Other LSD1 inhibitors include, but are not limited to those, e.g., disclosed in Ueda et al. ((2009) J. Am. Chem. Soc. 131(48):17536-17537) including; Binda et al. (J Am Chem. Soc. 2010 May 19; 132(19):6827-33). Mimasu et al. ((2010) Biochemistry June 22. [Epub ahead of print] PMID: 20568732 [PubMed—as supplied by publisher].

Other phenylcyclopropylamine derivatives and analogs are found, e.g., in Kaiser et al. ((1962) J. Med. Chem. 5:1243-1265); Zirkle et al. ((1962) J. Med. Chem. 1265-1284; U.S. Pat. Nos. 3,365,458; 3,471,522; 3,532,749) and Bolesov et al. ((1974) Zhurnal Organicheskoi Khimii 10:8 1661-1669) and Russian Patent No. 230169 (19681030).

Preferably, the LSD1 inhibitor for use in the invention is a selective LSD1 inhibitor or dual inhibitor of LSD1 and MAOB. In one preferred aspect, the selective LSD1 or dual LSD1 MAOB inhibitor has a molecular weight of less than 700. In one preferred aspect, the selective LSD1 or dual LSD1 MAOB inhibitor has a molecular weight of less than 500. In one preferred aspect, the selective LSD1 or dual selective LSD1 MAOB inhibitor has a molecular weight of less than 300.

Preferably, the LSD1 inhibitor comprises five or less amide bonds (—NH—C=O). Preferably, the LSD1 inhibitor comprises three or less amide bonds (—NH—C=O).

In one preferred aspect, the LSD1 inhibitor has zero amide bonds (—NH—C=O).

In one aspect, the selective LSD1 and dual selective LSD1/MAOB inhibitors for use in the invention desirably inhibits LSD1 and/or MAOB selectively compared to MAOA, thus avoiding deleterious side effects associated with administration to animals, including humans, of MAOA inhibitors. As the inventors have described herein, the selective LSD1 inhibitors and the dual LSD1/MAOB inhibitors can be administered in a such a way to an individual, e.g., a mammal or human, to achieve concentration in vivo that are expected to inhibit LSD1 and/or MAO-B while avoiding the toxicity associated with inhibition of MAOA and these concentrations are sufficient enough to improve specific phenotypes or symptoms associated with Hepadnaviridae infection or HBV infection.

In another aspect, the selective LSD1 and dual LSD1/MAOB inhibitors for use in the invention desirably inhibit LSD1 and/or MAOB targeting a host cell protein involved in Hepadnaviridae infection. Without wishing to be bound by theory targeting Hepadnaviridae with LSD1 inhibitors can avoid or lessen the ability of the virus to develop resistance to therapy alone or in combination with an interferon agent. As the inventors have described herein, the selective LSD1 inhibitors and the dual selective LSD1/MAOB inhibitors can be administered in a such a way to an individual, e.g., a mammal or human, to achieve concentration in vivo that are expected to inhibit LSD1 and/or MAO-B while avoiding the toxicity associated with inhibition of MAOA and these concentrations are sufficient enough to improve specific phenotypes or symptoms associated with Hepadnaviridae or HBV infection.

In still another aspect, the selective LSD1 and dual LSD1/MAOB inhibitors for use in the invention desirably inhibit LSD1 and/or MAOB targeting a host cell protein involved in HCV infection. Without wishing to be bound by theory targeting HBV with LSD1 inhibitors can avoid or lessen the side effects associated with treatment with interferon agent or an agent targeting a viral protein such as a DNA polymerase inhibitor. As the inventors have described herein, the selective LSD1 inhibitors and the dual LSD1/MAOB inhibitors can be administered in a such a way to an individual, e.g., a mammal or human, to achieve concentration in vivo that are expected to inhibit LSD1 and/or MAO-B while avoiding the toxicity associated with inhibition of MAOA and these concentrations are sufficient enough to improve specific phenotypes or symptoms associated with HBV infection.

The invention provides a pharmaceutical composition comprising a pharmaceutically acceptable carrier and a compound which is a selective inhibitor of LSD1. Preferably, LSD1 selective inhibitors have IC50 values for LSD1 which are at least 2-fold lower than the IC50 value for MAOA and/or MAOB. Even more preferably, LSD1 selective inhibitors have IC50 values for LSD1 which are at least 5-fold lower than the IC50 value for MAOA and/or MAOB. Yet even more preferably, LSD1 selective inhibitors have IC50 values for LSD1 which are at least 10-fold lower than the IC50 value for MAOA and/or MAOB. In one specific embodiment, dual selective LSD1/selective inhibitor for use in the invention are as defined above and is chosen from a phenylcyclopropylamine derivative or analog, a phenelzine derivative or analog, or a propargylamine derivative or homolog.

The invention also provides a pharmaceutical composition comprising a pharmaceutically acceptable carrier and a compound which is a dual inhibitor selective for LSD1 and MAOB. Preferably, dual LSD1/MAOB selective inhibitors have IC50 values for LSD1 and MAOB which are at least 2-fold lower than the IC50 value for MAO-A. Even more preferably, dual LSD1/MAOB selective inhibitors have IC50 values for LSD1 and MAOB which are at least 5-fold lower than the IC50 value for MAO-A. Yet even more preferably, dual LSD1/MAOB selective inhibitors have IC50 values for LSD1 and MAOB which are at least 10-fold lower than the IC50 value for MAO-A. In one specific embodiment, dual selective LSD1/selective inhibitors for use in the invention are as defined above and are chosen from a phenylcyclopropylamine derivative or analog, a phenelzine derivative or analog, or a propargylamine derivative or homolog.

Typically, compounds for use as selective LSD1 inhibitors or dual inhibitors of LSD1 and MAOB can be effective at an amount of from about 0.01 µg/kg to about 100 mg/kg per day based on total body weight. The active ingredient may be administered at once, or may be divided into a number of smaller doses to be administered at predetermined intervals of time. The suitable dosage unit for humans for each administration can be, e.g., from about 1 µg to about 2000 mg, preferably from about 5 µg to about 1000 mg, and even more preferably from about 0.5 mg to about 500 mg. The active ingredient can be administered orally or by other routes of administration, e.g., IP, IV, etc. Preferably, the inhibitor is formulated and delivered in such a way as to achieve concentration in vivo that modulate the target activity, e.g., LSD1 and/or MAOB. Thus, in a specific embodiment, the effective amount of compound ranges from 0.05 µg/kg to about 100 mg/kg, preferably from 0.05 µg/kg to about 50 mg/kg.

It should be understood that the dosage ranges set forth above are exemplary only and are not intended to limit the scope of this invention unless specified. The therapeutically effective amount for each active compound can vary with factors including but not limited to the activity of the compound used, stability of the active compound in the patient's body, the severity of the conditions to be alleviated, the total weight of the patient treated, the route of administration, the ease of absorption, distribution, and excretion of the active compound by the body, the age and sensitivity of the patient to be treated, and the like, as will be apparent to a skilled artisan. The amount of administration can be adjusted as the various factors change over time.

For oral delivery, the active compounds can be incorporated into a formulation that includes pharmaceutically acceptable carriers such as binders (e.g., gelatin, cellulose, gum tragacanth), excipients (e.g., starch, lactose), lubricants (e.g., magnesium stearate, silicon dioxide), disintegrating agents (e.g., alginate, Primogel, and corn starch), and sweetening or flavoring agents (e.g., glucose, sucrose, saccharin, methyl salicylate, and peppermint). The formulation can be orally delivered in the form of enclosed gelatin capsules or compressed tablets. Capsules and tablets can be prepared in any conventional techniques. The capsules and tablets can also be coated with various coatings known in the art to modify the flavors, tastes, colors, and shapes of the capsules and tablets. In addition, liquid carriers such as fatty oil can also be included in capsules.

Suitable oral formulations can also be in the form of suspension, syrup, chewing gum, wafer, elixir, and the like. If desired, conventional agents for modifying flavors, tastes, colors, and shapes of the special forms can also be included. In addition, for convenient administration by enteral feeding tube in patients unable to swallow, the active compounds can be dissolved in an acceptable lipophilic vegetable oil vehicle such as olive oil, corn oil and safflower oil.

The active compounds can also be administered parenterally in the form of solution or suspension, or in lyophilized form capable of conversion into a solution or suspension form before use. In such formulations, diluents or pharmaceutically acceptable carriers such as sterile water and physiological saline buffer can be used. Other conventional solvents, pH buffers, stabilizers, anti-bacteria agents, surfactants, and anti-oxidants can all be included. For example, useful components include sodium chloride, acetates, citrates or phosphates buffers, glycerin, dextrose, fixed oils, methyl parabens, polyethylene glycol, propylene glycol, sodium bisulfate, benzyl alcohol, ascorbic acid, and the like. The parenteral formulations can be stored in any conventional containers such as vials and ampoules.

Routes of topical administration include nasal, buccal, mucosal, rectal, or vaginal applications. For topical administration, the active compounds can be formulated into lotions, creams, ointments, gels, powders, pastes, sprays, suspensions, drops and aerosols. Thus, one or more thickening agents, humectants, and stabilizing agents can be included in the formulations. Examples of such agents include, but are not limited to, polyethylene glycol, sorbitol, xanthan gum, petrolatum, beeswax, or mineral oil, lanolin, squalene, and the like. A special form of topical administration is delivery by a transdermal patch. Methods for preparing transdermal patches are disclosed, e.g., in Brown, et al. (1988) Ann. Rev. Med. 39:221-229, which is incorporated herein by reference.

Subcutaneous implantation for sustained release of the active compounds may also be a suitable route of administration. This entails surgical procedures for implanting an active compound in any suitable formulation into a subcutaneous space, e.g., beneath the anterior abdominal wall. See, e.g., Wilson et al. (1984) J. Clin. Psych. 45:242-247. Hydrogels can be used as a carrier for the sustained release of the active compounds. Hydrogels are generally known in the art. They are typically made by crosslinking high molecular weight biocompatible polymers into a network, which swells in water to form a gel like material. Preferably, hydrogels are biodegradable or biosorbable. For purposes of this invention, hydrogels made of polyethylene glycols, collagen, or poly (glycolic-co-L-lactic acid) may be useful. See, e.g., Phillips et al. (1984) J. Pharmaceut. Sci., 73: 1718-1720.

The active compounds can also be conjugated; to a water soluble non-immunogenic non-peptidic high molecular weight polymer to form a polymer conjugate. For example, an active compound is covalently linked to polyethylene glycol to form a conjugate. Typically, such a conjugate exhibits improved solubility, stability, and reduced toxicity and immunogenicity. Thus, when administered to a patient, the active compound in the conjugate can have a longer half-life in the body, and exhibit better efficacy. See generally, Burnham (1994) Am. J. Hosp. Pharm. 15:210-218. PEGylated proteins are currently being used in protein replacement therapies and for other therapeutic uses. For example, PEGylated interferon (PEG-INTRON A®) is clinically used for treating Hepatitis B. PEGylated adenosine deaminase (ADAGEN®) is being used to treat severe combined immunodeficiency disease (SCIDS). PEGylated L-asparaginase (ONCAPSPAR®) is being used to treat acute lymphoblastic leukemia (ALL). It is preferred that the covalent linkage between the polymer and the active compound and/or the polymer itself is hydrolytically degradable under physiological conditions. Such conjugates known as "prodrugs" can readily release the active compound inside the body. Controlled release of an active compound can also be achieved by incorporating the active ingredient into microcapsules, nanocapsules, or hydrogels generally known in the art. Other pharmaceutically acceptable prodrugs of the compounds of this invention include, but are not limited to, esters, carbonates, thiocarbonates, N-acyl derivatives, N-acyloxyalkyl derivatives, quaternary derivatives of tertiary amines, N-Mannich bases, Schiff bases, amino acid conjugates, phosphate esters, metal salts and sulfonate esters.

Liposomes can also be used as carriers for the active compounds of the present invention. Liposomes are micelles made of various lipids such as cholesterol, phospholipids, fatty acids, and derivatives thereof. Various modified lipids can also be used. Liposomes can reduce the toxicity of the active compounds, and increase their stability. Methods for preparing liposomal suspensions containing active ingredients therein are generally known in the art. See, e.g., U.S. Pat. No. 4,522,811; Prescott, Ed., Methods in Cell Biology, Volume XIV, Academic Press, New York, N.Y. (1976).

The active ingredient can be formulated as a pharmaceutically acceptable salt. A "pharmaceutically acceptable salt" is intended to mean a salt that retains the biological effectiveness of the free acids and bases of the specified compound and that is not biologically or otherwise undesirable. A compound for use in the invention may possess a sufficiently acidic, a sufficiently basic, or both functional groups, and accordingly react with any of a number of inorganic or organic bases, and inorganic and organic acids, to form a pharmaceutically acceptable salt. Exemplary pharmaceutically acceptable salts include those salts prepared by reaction of the compounds of the present invention with a mineral or organic acid or an inorganic base, such as salts including sulfates, pyrosulfates, bisulfates, sulfites, bisulfites, phosphates, monohydrophosphates, dihydrophosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4 dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, gamma-hydroxybutyrates, glycollates, tartrates, methane-sulfonates, propanesulfonates, naphthalene-1-sulfonates, naphthalene-2-sulfonates, or mandelates.

As used herein, a "pharmaceutically acceptable carrier" refers to a non-API (API refers to Active Pharmaceutical Ingredient) substances such as disintegrators, binders, fillers, and lubricants used in formulating pharmaceutical products. They are generally safe for administering to humans according to established governmental standards, including those promulgated by the United States Food and Drug Administration and the European Medical Agency.

The active compounds can also be administered in combination with another active agent that synergistically treats or prevents the same symptoms or is effective for another disease or symptom in the patient treated so long as the other active agent does not interfere with or adversely affect the effects of the active compounds of this invention. Such other active agents include but are not limited to anti-inflammation agents, antiviral agents, antibiotics, antifungal agents, antithrombotic agents, cardiovascular drugs, cholesterol lowering agents, anti-cancer drugs, hypertension drugs, and the like.

As used herein the term "hepatitis B" or "HBV" refers to any of the strains and isolates of hepatitis B that have been identified or are identifiable according to known classifications. The term "hepatitis B" or "HBV" is intended to encompass all currently known strains, types and subtypes of HBV as wells those discovered and classified as HBV in the future. The identification of HBV is well within the purvey of an ordinary skilled artisan. Numerous HBV strains, types, and subtypes are known with their sequences being deposited in public databases.

As used herein, the term "diagnosed with HBV" refers to an individual in which a HBV marker has been detected. A variety of HBV markers are known in the art and can be readily measured by a skilled artisan. For example, HBV can be detected by testing for antibodies against HBV proteins (anti-HBV) in a patient or suspected carrier's blood serum. Another approach to detecting HBV is to test for HBV DNA in the serum of a patient or suspected carrier using a PCR based assay. Recombinant immunoblots can also be used to detect HBV. In this test serum is incubated with four recombinant viral proteins that are blotted on nitrocellulose strips. A simple color change indicates antibodies are present in the serum that bind to the viral proteins. Furthermore, new methods for detecting HBV are continually being developed and the methods can be employed for diagnosing HBV infection.

As used herein, the term "alleviate or ameliorate a symptom associated with HBV infection" refers to a lessening of: jaundice, fatigue, abdominal pain, loss of appetite, nausea, vomiting, malaise, fever, and joint pain. Also included within the scope of this term is a lessening or improvement in the level of an HBV marker, e.g., HBV protein detected in an immunoassay.

As used herein, the term "interferon agent" or "alpha interferon" or "interferon alpha" or "a-interferon" refers to the family of interferon proteins that inhibit viral replication, inhibit cellular proliferation, and modulate immune response. The term "alpha interferon" encompasses a variety of commercially available alpha interferons, including, but not limited to, Roferon A interferon (Hoffman-La Roche, Nutley, N.J.), Berofor alpha 2 (Boehringer Ingelheim Pharmaceutical, Inc., Ridgefield, Conn.), Sumiferon (Sumitomo, Japan), Wellferon interferon alpha-n1 (Glaxo-Wellcome Ltd., London, Great Britain). Alpha interferon 2b currently has the broadest approval throughout the world for use in treating HBV. U.S. Pat. No. 4,530,901 (which is hereby incorporated by reference in its entirety) provides a description of the manufacture of alpha interferon 2b.

As used herein, the term "side effects of interferon treatment" include fatigue, muscle aches, headaches, nausea, vomiting, low-grade fever, weight loss, irritability, depression, mild bone marrow suppression, and hair loss.

As used herein, the term "lamivudine" refers to the drug known as 3TC and has a chemical name of (2R, cis)-4-amino-1-(2-hydroxymethyl-1,3-oxathiolan-5-yl)-(1H)-pyrimidin-2-one. It is also known as (−) 2',3'-dideoxy, 3'-thiacytidine.

As used herein, the term "side effects of lamivudine treatment" refers to nausea, vomiting, headaches, hair loss, peripheral neuropathy, and pancreatitis associated with treatment with lamivudine.

As used herein, the term "alleviate a symptom associated with HBV" refers to a lessening of fatigue, dark urine, abdominal pain, nausea, tenderness in the upper right quadrant, poor appetite, muscle and joint pain, cirrhosis (with symptoms such as enlarged liver, enlarged spleen, jaundice, muscle wasting excoriations, ascites and ankle swelling).

The term also encompasses symptoms not associated with the liver, including, but not limited to, cryoglobulinemia symptoms such as skin rashes, joint and muscle aches, kidney disease, neuropathy, cryoglobulins, rheumatoid factor, low complement levels in serum, glomerulonephritis, or porphyria cutanea tarda. The term is also meant to encompass the alleviation of symptoms associated with disease that are thought to be or might be associated with chronic HBV including seronegative arthritis, keratoconjunctivitis sicca (Sjogren's syndrome), non-Hodgkin's type B-cell lymphomas, fibromyalgia, or lichen planus.

As used herein, the term "reversible amine oxidase" inhibitor refers to the class of compounds that inhibit MAOA or MAOB in a reversible manner that are well known in the art. Reversible amine oxidase inhibitors can be designed to increase selectivity for LSD1 using medicinal chemistry approaches.

As used herein, the term "irreversible amine oxidase" inhibitor refers to the class of compounds that inhibit MAOA or MAOB in an irreversible manner that are well known in the art. Examples of irreversible MAO inhibitors include phenylcyclopropylamine, phenelzine, and pargyline. Irreversible amine oxidase inhibitors can be designed to increase selectivity for LSD1 using medicinal chemistry approaches.

As used herein, the term "individual in need of treatment" encompasses individuals who have symptoms of HBV infection, those who have been diagnosed with HBV, or those in need of prophylaxis. An "individual in need of treatment" can have anti-HBV, HBV RNA, elevated serum aminotransferase levels, and/or evidence of chronic hepatitis.

EXAMPLES

Example 1

Biochemical Assays

Compounds for use in the methods of the invention can be identified by their ability to inhibit LSD1. The ability of the compounds of the invention to inhibit LSD1 can be tested as follows. Human recombinant LSD1 protein was purchased from BPS Bioscience Inc. In order to monitor LSD1 enzymatic activity and/or its inhibition rate by our inhibitor(s) of interest, di-methylated H3-K4 peptide (Millipore) was chosen as a substrate. The demethylase activity was estimated, under aerobic conditions, by measuring the release of $H_2O_2$ produced during the catalytic process, using the Amplex® Red peroxide/peroxidase-coupled assay kit (Invitrogen).

Briefly, a fixed amount of LSD1 was incubated on ice for 15 minutes, in the absence and/or in the presence of various concentrations of inhibitor (e.g., from 0 to 75 µM, depending on the inhibitor strength). Tranylcypromine (Biomol International) was used as a control for inhibition. Within the experiment, each concentration of inhibitor was tested in triplicate. After leaving the enzyme interacting with the inhibitor, 12.5 µM of di-methylated H3-K4 peptide was added to each reaction and the experiment was left for 1 hour at 37° C. in the dark. The enzymatic reactions were set up in a 50 mM sodium phosphate, pH 7.4 buffer. At the end of the incubation, Amplex® Red reagent and horseradish peroxidase (HPR) solution were added to the reaction according to the recommendations provided by the supplier (Invitrogen), and left to incubate for 30 extra minutes at room temperature in the dark. A 1 µM $H_2O_2$ solution was used as a control of the kit efficiency. The conversion of the Amplex® Red reagent to resorufin due to the presence of $H_2O_2$ in the assay, was monitored by fluorescence (excitation at 540 nm, emission at 590 nm) using a microplate reader (Infinite 200, Tecan). Arbitrary units were used to measure level of $H_2O_2$ produced in the absence and/or in the presence of inhibitor.

The maximum demethylase activity of LSD1 was obtained in the absence of inhibitor and corrected for background fluorescence in the absence of LSD1. The Ki (IC50) of each inhibitor was estimated at half of the maximum activity.

Human recombinant monoamine oxidase proteins MAO-A and MAO-B were purchased from Sigma Aldrich. MAOs catalyze the oxidative deamination of primary, secondary and tertiary amines. In order to monitor MAO enzymatic activities and/or their inhibition rate by inhibitor(s) of interest, a fluorescent-based (inhibitor)-screening assay was set up. 3-(2-Aminophenyl)-3-oxopropanamine (kynuramine dihydrobromide, Sigma Aldrich), a non fluorescent compound was chosen as a substrate. Kynuramine is a non-specific substrate for both MAOs activities. While undergoing oxidative deamination by MAO activities, kynuramine is converted into 4-hydroxyquinoline (4-HQ), a resulting fluorescent product.

The monoamine oxidase activity was estimated by measuring the conversion of kynuramine into 4-hydroxyquinoline. Assays were conducted in 96-well black plates with clear bottom (Corning) in a final volume of 100 µL. The assay buffer was 100 mM HEPES, pH 7.5. Each experiment was performed in triplicate within the same experiment.

Briefly, a fixed amount of MAO (0.25 µg for MAO-A and 0.5 µg for MAO-B) was incubated on ice for 15 minutes in the reaction buffer, in the absence and/or in the presence of various concentrations of inhibitor (e.g., from 0 to 50 µM, depending on the inhibitor strength). Tranylcypromine (Biomol International) was used as a control for inhibition.

After leaving the enzyme(s) interacting with the inhibitor, 60 to 90 µM of kynuramine was added to each reaction for MAO-B and MAO-A assay respectively, and the reaction was left for 1 hour at 37° C. in the dark. The oxidative deamination of the substrate was stopped by adding 50 µL (v/v) of NaOH 2N. The conversion of kynuramine to 4-hydroxyquinoline, was monitored by fluorescence (excitation at 320 nm, emission at 360 nm) using a microplate reader (Infinite 200, Tecan). Arbitrary units were used to measure levels of fluorescence produced in the absence and/or in the presence of inhibitor.

The maximum of oxidative deamination activity was obtained by measuring the amount of 4-hydroxyquinoline formed from kynuramine deamination in the absence of inhibitor and corrected for background fluorescence in the absence of MAO enzymes. The Ki (IC50) of each inhibitor was determined at Vmax/2.

Example 2

LSD1 and LSD1/MAOB Dual Inhibitors

| Compound No. | LSD1 IC50 (uM) | MAOA IC50 (uM) | MAO B IC50 (uM) |
|---|---|---|---|
| Dual-1 | <0.20 | >1.0 | <0.20 |
| Dual-2 | <0.20 | >40 | <0.30 |
| Selective-1 | <0.10 | >1.0 | >1.0 |
| Selective-2 | <0.10 | >1.0 | >1.0 |

Other specific examples of LSD1 inhibitors include Compound X

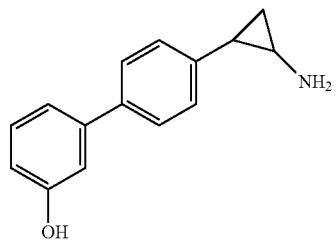 [SMILES: NC1CC1c1ccc(-c2cccc(O)c2)cc1]

Compound Y

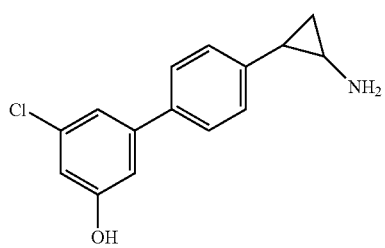 [SMILES: NC1CC1c1ccc(-c2cc(O)cc(Cl)c2)cc1]

which are both selective LSD1 inhibitors
or Compound Z

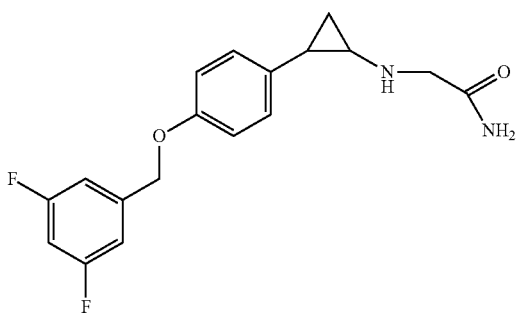 [SMILES: NC(=O)CNC1CC1c1ccc(OCc2cc(F)cc(F)c2)cc1]

which is a dual LSD1/MAOB inhibitor.

Example 3

LSD1 and LSD1/MAO-B Dual Inhibitors Decrease Histone Lysine Methylation in Cell Based Assays Histone from SH-SY5Y cells grown in the presence of Compound Dual-1 (a dual LSD17MAOB inhibitor) or tranylcypromine (parnate) for 1, 2, and 3 days were extracted and subjected to western blot analysis using a commercially available antibody specific dimethylated H.K4. B-actin was used as a loading control.

The results of a western blot stained for H3K4 methylation with SH-SY5Y cells grown in the presence of Compound Dual-1 or tranylcypromine (parnate) for 1, 2, and 3 days, showing that this compound increase H3K4 methylation in cells in a time dependent manner and furthermore Compound Dual-1 appears to be 10-fold or more potent at increasing global H3K4 levels as compared to tranylcypromine.

Furthermore, the inventors have conducted similar studies for other dual inhibitors of LSD1/MAOB and with selective LSD1 inhibitors and found that these compounds can increase dimethylated H3K4 levels in similarly performed assays.

Example 4

LSD1 Inhibitors can be Administered Safely to Mammals

Maximum tolerated dose studies and pharmacokinetics for several LSD1 inhibitors were assessed to determine if the compound can be administered to mammals safely at does that are expected to achieve therapeutic effects. In particular, compound X was given to mice IP at 20 mg/kg 40 mg/kg and 60 mg/kg daily for 10 days in a MTD study conducted at Leitat. The results of these studies should that these doses were tolerated with acceptable toxicity. Furthermore, PK studies showed that such doses achieved Cmax value that are expected to result in therapeutic levels of LSD1 inhibitor in mammals.

Example 5

LSD1 Inhibitors Inhibit HBV DNA Replication

Anti-HBV assays were conducted at Southern Research Organization using an HBV DNA replicon with a luciferase reporter.

Southern Research reports HepG2-2.2.15 is a stable cell line containing the hepatitis B virus (HBV) ayw strain genome. Antiviral compounds blocking any late step of viral replication such as transcription, translation, pregenome encapsidation, reverse transcription, particle assembly and release can be identified and characterized using this cell line. Initially we test whether a compound will reduce the production of secreted HBV from cells utilizing our real time quantitative PCR (TaqMan) HBV DNA assay.

TABLE 1

Activity of LSD1 inhibitor in an anti-HBV assay with HepG2-2.2.15 cells

| Compound | High Test Concentration | Antiviral Activity $EC_{50}$ | Cytotoxicity $IC_{50}$ | Selectivity Index $SI_{50}$ |
|---|---|---|---|---|
| Compound X | 100 uM | 2.24 uM | 54.81 uM | 26.8 |
| 3TC | 1 | 0.01 uM | 60.4 uM | >100 |

What is claimed is:

1. A method of treating a Hepadnaviridae infection or a disease or disorder associated with Hepadnaviridae chosen from Hepatitis B and liver cancer, the method comprising administering to an individual in need of such treatment a therapeutically effective amount of an LSD1 (lysine specific demethylase-1) inhibitor, wherein the LSD1 inhibitor is a phenylcyclopropylamine derivative or analog, a phenelzine derivative or analog, or a propargylamine derivative or analog.

2. The method according to claim 1, wherein the Hepadnaviridae infection is a Hepatitis B virus (HBV) infection.

3. The method according to claim 1, wherein the Hepadnaviridae infection is a Hepatitis B virus infection resistant to one or more DNA polymerases inhibitors.

4. The method according to claim 1, wherein the LSD1 inhibitor is a reversible or irreversible amine oxidase inhibitor.

5. The method according to claim 1, wherein the LSD1 inhibitor inhibits Hepadnaviridae DNA replication.

6. The method according to claim 1, wherein the LSD1 inhibitor is a phenylcyclopropylamine derivative or analog.

7. The method according to claim 1, wherein the LSD1 inhibitor has a therapeutic index of 10 or greater.

8. The method according to claim 1, wherein the LSD1 inhibitor has a therapeutic index of 20 or greater.

9. The method according to claim 2, further comprising administering to the individual an additional therapeutic agent, wherein said additional therapeutic agent is an anti-HBV agent.

10. The method according to claim 9, wherein the additional therapeutic agent is an interferon agent or a DNA polymerase inhibitor.

11. The method according to claim 1, wherein the phenelzine derivative or analog:
    (a) has one, two, three, four or five substituents on the phenyl group;
    (b) has the phenyl group substituted with (exchanged for) an aryl or heterocyclyl group, wherein the aryl or heterocyclyl group has zero, one, two, three, four or five substituents; or
    (c) as in (a) or (b) and wherein the phenylzine derivative or analog has a substitution on the terminal nitrogen of the hydrazine group.

12. The method according to claim 1, wherein the propargylamine derivative or analog is a pargyline derivative or analog, and wherein:
    (a) the pargyline derivative or analog has one, two, three, four or five substituents on the phenyl group;
    (b) the pargyline derivative or analog has the phenyl group substituted with (exchanged for) an aryl or heterocyclyl group wherein the aryl or heterocyclyl group has zero, one, two, three, four or five substituents; or
    (c) as in (a) or (b) and wherein the propargylamine moiety of pargyline has one or two substituents.

13. The method according to claim 6, wherein the phenylcyclopropylamine derivative or analog:
    (a) has one, two, three, four or five substituents on the phenyl group;
    (b) has the phenyl group substituted with (exchanged for) an aryl or heterocyclyl group, wherein the aryl or heterocyclyl group has zero, one, two, three, four or five substituents; or
    (c) as in (a) or (b) and wherein the phenycyclopropylamine derivative or analog has one or two substituents on the amino group of the cyclopropylamine core.

14. The method according to claim 1, wherein the phenylcyclopropylamine derivative or analog:
    (a) has one, two, three, four or five substituents on the phenyl group;
    (b) has the phenyl group substituted with (exchanged for) an aryl or heterocyclyl group, wherein the aryl or heterocyclyl group has zero, one, two, three, four or five substituents; or
    (c) as in (a) or (b) and wherein the phenycyclopropylamine derivative or analog has one or two substituents on the amino group of the cyclopropylamine core.

15. The method according to claim 6, wherein the phenylcyclopropylamine derivative or analog is selected from:
    N-cyclopropyl-2-{[(trans)-2-phenylcyclopropyl]amino}acetamide;
    2-{[(trans)-2-phenylcyclopropyl]amino}acetamide;
    N-cyclopropyl-2-{[(trans)-2-phenylcyclopropyl]amino}propanamide;
    2-{[(trans)-2-phenylcyclopropyl]amino}-N-prop-2-ynylacetamide;
    N-isopropyl-2-{[(trans)-2-phenylcyclopropyl]amino}acetamide;
    N-(tert-butyl)-2-{[(trans)-2-phenylcyclopropyl]amino}acetamide;
    N-(2-morpholin-4-yl-2-oxoethyl)-N-[(trans)-2-phenylcyclopropyl]amine;
    2-{[(trans)-2-phenylcyclopropyl]amino}propanamide;
    Methyl 2-{[(trans)-2-phenylcyclopropyl]amino}propanoate;
    1-(4-methylpiperazin-1-yl)-2-((trans)-2-phenylcyclopropylamino)ethanone;
    1-(4-ethylpiperazin-1-yl)-2-((trans)-2-phenylcyclopropylamino)ethanone;
    1-(4-benzylpiperazin-1-yl)-2-((trans)-2-phenylcyclopropylamino)ethanone;
    2-((trans)-2-phenylcyclopropylamino)-1-(4-phenylpiperazin-1-yl)ethanone;
    2-((trans)-2-(4-(benzyloxy)phenyl)cyclopropylamino)-1-(4-methylpiperazin-1-yl)ethanone;
    2-((trans)-2-(1,1'-biphenyl-4-yl)cyclopropylamino)-1-(4-methylpiperazin-1-yl)ethanone;
    2-((trans)-2-(4-(benzyloxy)phenyl)cyclopropylamino)-N-cyclopropylacetamide;
    2-((trans)-2-(4-(3-fluorobenzyloxy)phenyl)cyclopropylamino)-1-(4-methylpiperazin-1-yl)ethanone;
    2-((trans)-2-(4-(4-fluorobenzyloxy)phenyl)cyclopropylamino)-1-(4-methylpiperazin-1-yl)ethanone;
    2-((trans)-2-(4-(3-chlorobenzyloxy)phenyl)cyclopropylamino)-1-(4-methylpiperazin-1-yl)ethanone;
    1-(4-methylpiperazin-1-yl)-2-((trans)-2-(4-phenethoxyphenyl)cyclopropylamino)ethanone;
    2-((trans)-2-(biphenyl-4-yl)cyclopropylamino)-1-(4-methylpiperazin-1-yl)ethanone;
    N-cyclopropyl-2-{[(trans)-2-phenylcyclopropyl]amino}acetamide;
    N-methyl-trans-2-(Phenylcyclopropylamino)propanamide;
    2-{methyl[(trans)-2-phenylcyclopropyl]amino}acetamide;
    N-[2-(4-methylpiperazin-1-yl)ethyl]-N-[(trans)-2-phenylcyclopropyl] amine;
    N-cyclopropyl-N'-[(trans)-2-phenylcyclopropyl]ethane-1,2-diamine;
    N,N-dimethyl-N'-(2-{[(trans)-2-phenylcyclopropyl]amino}ethyl)ethane-1,2-diamine;
    (3R)-1-(2-{[(trans)-2-phenylcyclopropyl]amino}ethyl)pyrrolidin-3-amine;
    (3S)-N,N-dimethyl-1-(2-{[(trans)-2-phenylcyclopropyl]amino}ethyl)pyrrolidin-3-amine;
    (3R)-N,N-dimethyl-1-(2-{[(trans)-2-phenylcyclopropyl]amino}ethyl)pyrrolidin-3-amine;
    N-[(trans)-2-phenylcyclopropyl]-N-(2-piperazin-1-ylethyl)amine;
    N,N-diethyl-N'-[(trans)-2-phenylcyclopropyl]ethane-1,2-diamine;
    N-[(trans)-2-phenylcyclopropyl]-N-(2-piperidin-1-ylethyl)amine;
    (trans)-2-(4-(benzyloxy)phenyl)-N-(2-(4-methylpiperazin-1-yl)ethyl)cyclopropanamine;
    (trans)-N-(2-(4-methylpiperazin-1-yl)ethyl)-2-(3'-(trifluoromethyl)biphenyl-4-yl)cyclopropanamine;
    (trans)-2-(3'-chlorobiphenyl-4-yl)-N-(2-(4-methylpiperazin-1-yl)ethyl)cyclopropanamine;
    (R)-1-(2-((trans)-2-(3'-(trifluoromethyl)biphenyl-4-yl)cyclopropylamino)ethyl)pyrrolidin-3-amine;

N1-cyclopropyl-N2-((trans)-2-(3'-(trifluoromethyl)biphenyl-4-yl)cyclopropyl)ethane-1,2-diamine;
N-4-fluorobenzyl-N-{(trans)-2-[4-(benzyloxy)phenyl]cyclopropyl}amine;
N-4-methoxybenzyl-N-{(trans)-2-[4-(benzyloxy)phenyl]cyclopropyl}amine;
N-benzyl-N-{(trans)-2-[4-(benzyloxy)phenyl]cyclopropyl}amine;
N-[(trans)-2-phenylcyclopropyl]amino-methyl)pyridin-3-ol;
N-[(trans)-2-phenylcyclopropyl]-N-(3-methylpyridin-2-ylmethyl)amine;
N-[(trans)-2-phenylcyclopropyl]-N-(4-chloropyridin-3-ylmethyl)amine;
N-[(trans)-2-phenylcyclopropyl]-N-(4-trifluoromethylpyridin-3-ylmethyl)amine;
N-(3-methoxybenzyl)-N-[(trans)-2-phenylcyclopropyl]amine;
N-[(trans)-2-phenylcyclopropyl]-N-(quinolin-4-ylmethyl)amine;
N-(2-fluorobenzyl)-N-[(trans)-2-phenylcyclopropyl]amine;
N-(3-fluorobenzyl)-N-[(trans)-2-phenylcyclopropyl]amine;
N-[(trans)-2-phenylcyclopropyl]-N-(3,4-dichloro-1-phenylmethyl)amine;
N-[(trans)-2-phenylcyclopropyl]-N-(5-bromo-thiophen-2-ylmethyl)amine;
N-[(trans)-2-phenylcyclopropyl]-N-(3-bromo-thiophen-2-ylmethyl)amine;
N-[(trans)-2-phenylcyclopropyl]-N-(thiophen-2-ylmethyl)amine;
N-[(trans)-2-phenylcyclopropyl]-N-(1,3-thiazol-2-ylmethyl)amine;
N-[(trans)-2-phenylcyclopropyl]-N-(3-methyl-pyridin-2-ylmethyl)amine;
N-[(trans)-2-phenylcyclopropyl]-N-(pyridin-4-ylmethyl)amine;
N-[(trans)-2-phenylcyclopropyl]-N-(pyridin-3-ylmethyl)amine;
N-[(trans)-2-phenylcyclopropyl]-N-(pyridin-2-ylmethyl)amine;
[(trans)-2-phenylcyclopropyl]-N-[4-(trifluoromethyl)benzyl]amine;
({[(trans)-2-phenylcyclopropyl]amino}methyl)benzonitrile;
N-(4-fluorobenzyl)-N-[(trans)-2-phenylcyclopropyl]amine;
N-[(trans)-2-phenylcyclopropyl]-N-(3-bromo-pyridin-2-ylmethyl)amine;
N-4-cyanobenzyl-N-{(trans)-2-[4-(benzyloxy)phenyl]cyclopropyl}amine;
N-4-[(benzyloxy)-benzyl]-N-[(trans)-2-(4-phenyl)cyclopropyl]amine;
2-((trans)-2-(4-(4-cyanobenzyloxy)phenyl)cyclopropylamino)acetamide;
2-((trans)-2-(4-(3-cyanobenzyloxy)phenyl)cyclopropylamino)acetamide;
2-((trans)-2-(4-(benzyloxy)phenyl)cyclopropylamino)acetamide;
2-((trans)-2-(4-(4-fluorobenzyloxy)phenyl)cyclopropylamino)acetamide;
2-((trans)-2-(4-(3-fluorobenzyloxy)phenyl)cyclopropylamino)acetamide;
2-((trans)-2-(4-(3-chlorobenzyloxy)phenyl)cyclopropylamino)acetamide;
2-((trans)-2-(4-(4-chlorobenzyloxy)phenyl)cyclopropylamino)acetamide;
2-((trans)-2-(4-(3-bromobenzyloxy)phenyl)cyclopropylamino)acetamide;
2-((trans)-2-(4-(3,5-difluorobenzyloxy)phenyl)cyclopropylamino)acetamide;
2-((trans)-2-(4-phenethoxyphenyl)cyclopropylamino)acetamide;
2-((trans)-2-(3'-(trifluoromethyl)biphenyl-4-yl)cyclopropylamino)acetamide;
2-((trans)-2-(3'-chlorobiphenyl-4-yl)cyclopropylamino)acetamide;

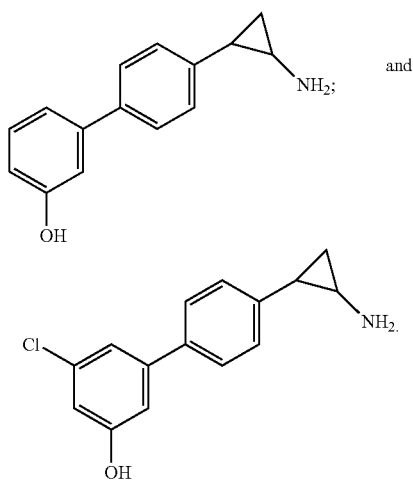

16. The method according to claim 2, wherein the LSD1 inhibitor is a phenylcyclopropylamine derivative or analog.

17. The method according to claim 16, wherein the phenylcyclopropylamine derivative or analog is selected from:
N-cyclopropyl-2-{[(trans)-2-phenylcyclopropyl]amino}acetamide;
2-{[(trans)-2-phenylcyclopropyl]amino}acetamide;
N-cyclopropyl-2-{[(trans)-2-phenylcyclopropyl]amino}propanamide;
2-{[(trans)-2-phenylcyclopropyl]amino}-N-prop-2-ynylacetamide;
N-isopropyl-2-{[(trans)-2-phenylcyclopropyl]amino}acetamide;
N-(tert-butyl)-2-{[(trans)-2-phenylcyclopropyl]amino}acetamide;
N-(2-morpholin-4-yl-2-oxoethyl)-N-[(trans)-2-phenylcyclopropyl]amine;
2-{[(trans)-2-phenylcyclopropyl]amino}propanamide;
Methyl 2-{[(trans)-2-phenylcyclopropyl]amino}propanoate;
1-(4-methylpiperazin-1-yl)-2-((trans)-2-phenylcyclopropylamino)ethanone;
1-(4-ethylpiperazin-1-yl)-2-((trans)-2-phenylcyclopropylamino)ethanone;
1-(4-benzylpiperazin-1-yl)-2-((trans)-2-phenylcyclopropylamino)ethanone;
2-((trans)-2-phenylcyclopropylamino)-1-(4-phenylpiperazin-1-yl)ethanone;
2-((trans)-2-(4-(benzyloxy)phenyl)cyclopropylamino)-1-(4-methylpiperazin-1-yl)ethanone;
2-((trans)-2-(1,1'-biphenyl-4-yl)cyclopropylamino)-1-(4-methylpiperazin-1-yl)ethanone;

2-((trans)-2-(4-(benzyloxy)phenyl)cyclopropylamino)-N-cyclopropylacetamide;
2-((trans)-2-(4-(3-fluorobenzyloxy)phenyl)cyclopropylamino)-1-(4-methylpiperazin-1-yl)ethanone;
2-((trans)-2-(4-(4-fluorobenzyloxy)phenyl)cyclopropylamino)-1-(4-methylpiperazin-1-yl)ethanone;
2-((trans)-2-(4-(3-chlorobenzyloxy)phenyl)cyclopropylamino)-1-(4-methylpiperazin-1-yl)ethanone;
1-(4-methylpiperazin-1-yl)-2-((trans)-2-(4-phenethoxyphenyl)cyclopropylamino)ethanone;
2-((trans)-2-(biphenyl-4-yl)cyclopropylamino)-1-(4-methylpiperazin-1-yl)ethanone;
N-cyclopropyl-2-{[(trans)-2-phenylcyclopropyl]amino}acetamide;
N-methyl-trans-2-(Phenylcyclopropylamino)propanamide;
2-{methyl[(trans)-2-phenylcyclopropyl]amino}acetamide;
N-[2-(4-methylpiperazin-1-yl)ethyl]-N-[(trans)-2-phenylcyclopropyl] amine;
N-cyclopropyl-N'-[(trans)-2-phenylcyclopropyl]ethane-1,2-diamine;
N,N-dimethyl-N'-(2-{[(trans)-2-phenylcyclopropyl]amino}ethyl)ethane-1,2-diamine;
(3R)-1-(2-{[(trans)-2-phenylcyclopropyl]amino}ethyl)pyrrolidin-3-amine;
(3S)-N,N-dimethyl-1-(2-{[(trans)-2-phenylcyclopropyl]amino}ethyl)pyrrolidin-3-amine;
(3R)-N,N-dimethyl-1-(2-{[(trans)-2-phenylcyclopropyl]amino}ethyl)pyrrolidin-3-amine;
N-[(trans)-2-phenylcyclopropyl]-N-(2-piperazin-1-yl-ethyl)amine;
N,N-diethyl-N'-[(trans)-2-phenylcyclopropyl]ethane-1,2-diamine;
N-[(trans)-2-phenylcyclopropyl]-N-(2-piperidin-1-yl-ethyl)amine;
(trans)-2-(4-(benzyloxy)phenyl)-N-(2-(4-methylpiperazin-1-yl)ethyl)cyclopropanamine;
(trans)-N-(2-(4-methylpiperazin-1-yl)ethyl)-2-(3'-(trifluoromethyl)biphenyl-4-yl)cyclopropanamine;
(trans)-2-(3'-chlorobiphenyl-4-yl)-N-(2-(4-methylpiperazin-1-yl)ethyl)cyclopropanamine;
(R)-1-(2-((trans)-2-(3'-(trifluoromethyl)biphenyl-4-yl)cyclopropylamino)ethyl)pyrrolidin-3-amine;
N1-cyclopropyl-N2-((trans)-2-(3'-(trifluoromethyl)biphenyl-4-yl)cyclopropyl)ethane-1,2-diamine;
N-4-fluorobenzyl-N-{(trans)-2-[4-(benzyloxy)phenyl]cyclopropyl}amine;
N-4-methoxybenzyl-N-{(trans)-2-[4-(benzyloxy)phenyl]cyclopropyl}amine;
N-benzyl-N-{(trans)-2-[4-(benzyloxy)phenyl]cyclopropyl}amine;
N-[(trans)-2-phenylcyclopropyl]amino-methyl)pyridin-3-ol;
N-[(trans)-2-phenylcyclopropyl]-N-(3-methylpyridin-2-ylmethyl)amine;
N-[(trans)-2-phenylcyclopropyl]-N-(4-chloropyridin-3-ylmethyl)amine;
N-[(trans)-2-phenylcyclopropyl]-N-(4-trifluoromethylpyridin-3-ylmethyl)amine;
N-(3-methoxybenzyl)-N-[(trans)-2-phenylcyclopropyl]amine;
N-[(trans)-2-phenylcyclopropyl]-N-(quinolin-4-ylmethyl)amine;
N-(2-fluorobenzyl)-N-[(trans)-2-phenylcyclopropyl]amine;
N-(3-fluorobenzyl)-N-[(trans)-2-phenylcyclopropyl]amine;
N-[(trans)-2-phenylcyclopropyl]-N-(3,4-dichloro-1-phenylmethyl)amine;
N-[(trans)-2-phenylcyclopropyl]-N-(5-bromo-thiophen-2-ylmethyl)amine;
N-[(trans)-2-phenylcyclopropyl]-N-(3-bromo-thiophen-2-ylmethyl)amine;
N-[(trans)-2-phenylcyclopropyl]-N-(thiophen-2-ylmethyl)amine;
N-[(trans)-2-phenylcyclopropyl]-N-(1,3-thiazol-2-ylmethyl)amine;
N-[(trans)-2-phenylcyclopropyl]-N-(3-methyl-pyridin-2-ylmethyl)amine;
N-[(trans)-2-phenylcyclopropyl]-N-(pyridin-4-ylmethyl)amine;
N-[(trans)-2-phenylcyclopropyl]-N-(pyridin-3-ylmethyl)amine;
N-[(trans)-2-phenylcyclopropyl]-N-(pyridin-2-ylmethyl)amine;
[(trans)-2-phenylcyclopropyl]-N-[4-(trifluoromethyl)benzyl]amine;
({[(trans)-2-phenylcyclopropyl]amino}methyl)benzonitrile;
N-(4-fluorobenzyl)-N-[(trans)-2-phenylcyclopropyl]amine;
N-[(trans)-2-phenylcyclopropyl]-N-(3-bromo-pyridin-2-ylmethyl)amine;
N-4-cyanobenzyl-N-{(trans)-2-[4-(benzyloxy)phenyl]cyclopropyl}amine;
N-4-[(benzyloxy)-benzyl]-N-[(trans)-2-(4-phenyl)cyclopropyl]amine;
2-((trans)-2-(4-(4-cyanobenzyloxy)phenyl)cyclopropylamino)acetamide;
2-((trans)-2-(4-(3-cyanobenzyloxy)phenyl)cyclopropylamino)acetamide;
2-((trans)-2-(4-(benzyloxy)phenyl)cyclopropylamino)acetamide;
2-((trans)-2-(4-(4-fluorobenzyloxy)phenyl)cyclopropylamino)acetamide;
2-((trans)-2-(4-(3-fluorobenzyloxy)phenyl)cyclopropylamino)acetamide;
2-((trans)-2-(4-(3-chlorobenzyloxy)phenyl)cyclopropylamino)acetamide;
2-((trans)-2-(4-(4-chlorobenzyloxy)phenyl)cyclopropylamino)acetamide;
2-((trans)-2-(4-(3-bromobenzyloxy)phenyl)cyclopropylamino)acetamide;
2-((trans)-2-(4-(3,5-difluorobenzyloxy)phenyl)cyclopropylamino)acetamide;
2-((trans)-2-(4-phenethoxyphenyl)cyclopropylamino)acetamide;
2-((trans)-2-(3'-(trifluoromethyl)biphenyl-4-yl)cyclopropylamino)acetamide;
2-((trans)-2-(3'-chlorobiphenyl-4-yl)cyclopropylamino)acetamide;

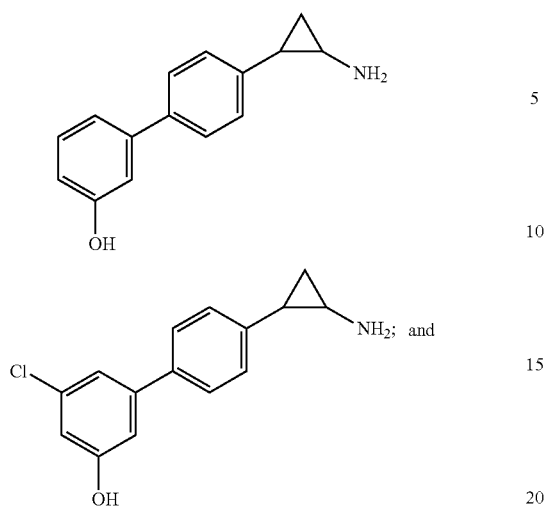

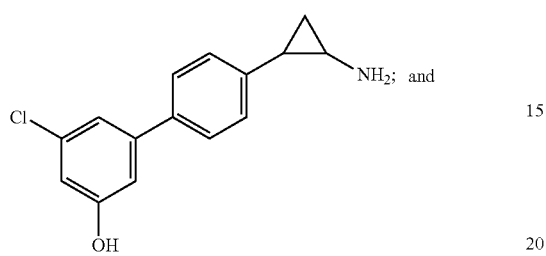

18. A method of treating HBV and Hepatitis C virus (HCV) co-infection, the method comprising administering to an individual in need of such treatment a therapeutically effective amount of an LSD1 inhibitor.

19. The method according to claim 18, wherein the LSD1 inhibitor has a therapeutic index of 10 or greater.

20. The method according to claim 18, further comprising administering to the individual an additional therapeutic agent, wherein said additional therapeutic agent is an anti-HCV agent or an anti-HBV agent.

* * * * *